(12) United States Patent
Demarais et al.

(10) Patent No.: US 7,873,417 B2
(45) Date of Patent: Jan. 18, 2011

(54) METHODS AND APPARATUS FOR PULSED ELECTRIC FIELD NEUROMODULATION VIA AN INTRA-TO-EXTRAVASCULAR APPROACH

(75) Inventors: Denise Demarais, Los Gatos, CA (US); Benjamin J. Clark, Redwood City, CA (US); Nicolas Zadno, Fremont, CA (US); Erik Thai, San Jose, CA (US); Hanson Gifford, III, Woodside, CA (US)

(73) Assignee: Ardian, Inc., Mountain View, CA (US)

( * ) Notice: Subject to any disclaimer, the term of this patent is extended or adjusted under 35 U.S.C. 154(b) by 0 days.

(21) Appl. No.: 12/616,708

(22) Filed: Nov. 11, 2009

(65) Prior Publication Data

US 2010/0057150 A1 Mar. 4, 2010

Related U.S. Application Data

(63) Continuation of application No. 11/363,867, filed on Feb. 27, 2006, now Pat. No. 7,620,451, which is a continuation-in-part of application No. 11/129,765, filed on May 13, 2005, now Pat. No. 7,653,438, which is a continuation-in-part of application No. 10/408,665, filed on Apr. 8, 2003, now Pat. No. 7,162,303, said application No. 11/363,867 is a continuation-in-part of application No. 11/189,563, filed on Jul. 25, 2005, and a continuation-in-part of application No. 11/266,993, filed on Nov. 4, 2005, now Pat. No. 7,756,583.

(60) Provisional application No. 60/813,589, filed on Dec. 29, 2005, provisional application No. 60/616,254, filed on Oct. 5, 2004, provisional application No. 60/624,793, filed on Nov. 2, 2004, provisional application No. 60/442,970, filed on Jan. 29, 2003, provisional application No. 60/415,575, filed on Oct. 3, 2002, provisional application No. 60/370,190, filed on Apr. 8, 2002.

(51) Int. Cl.
*A61N 1/05* (2006.01)

(52) U.S. Cl. ............... 607/40; 607/1; 607/2; 607/3; 607/9; 607/41; 607/72

(58) Field of Classification Search ............... 607/1–3, 607/9, 72
See application file for complete search history.

(56) References Cited

U.S. PATENT DOCUMENTS

| | | | |
|---|---|---|---|
| 6,328,699 B1 * | 12/2001 | Eigler et al. | 600/486 |
| 6,522,926 B1 * | 2/2003 | Kieval et al. | 607/44 |
| 2003/0216792 A1 | 11/2003 | Levin et al. | |
| 2005/0288730 A1 | 12/2005 | Deem et al. | |

FOREIGN PATENT DOCUMENTS

WO WO-97/13463 A1 4/1997

OTHER PUBLICATIONS

European Search Report; European Patent Application No. 06847926.0; Applicant; Ardian, Inc.; Date of Mailing; Feb. 10, 2010, 6 pages.

* cited by examiner

*Primary Examiner*—Carl H Layno
*Assistant Examiner*—Deborah Malamud
(74) *Attorney, Agent, or Firm*—Perkins Coie LLP

(57) ABSTRACT

Methods and apparatus are provided for pulsed electric field neuromodulation via an intra-to-extravascular approach, e.g., to effectuate irreversible electroporation or electrofusion, necrosis and/or inducement of apoptosis, alteration of gene expression, changes in cytokine upregulation and other conditions in target neural fibers. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

30 Claims, 19 Drawing Sheets

METHODS AND APPARATUS FOR PULSED ELECTRIC FIELD NEUROMODULATION VIA AN INTRA-TO-EXTRAVASCULAR APPROACH

CROSS REFERENCE TO RELATED APPLICATIONS

The present application is a continuation of U.S. patent application Ser. No. 11/363,867, filed Feb. 27, 2006, now U.S. Pat. No. 7,620,451, which claims the benefit of U.S. Provisional Application No. 60/813,589, filed on Dec. 29, 2005, the disclosures of which are incorporated herein by reference in their entirety. U.S. patent application Ser. No. 11/363,867, now U.S. Pat. No. 7,620,451, is also a continuation-in-part of each of the following U.S. Patent Applications:

(a) U.S. patent application Ser. No. 11/129,765, filed on May 13, 2005, now U.S. Pat. No. 7,653,438, which claims the benefit of U.S. Provisional Application Nos. 60/616,254, filed on Oct. 5, 2004; and 60/624,793, filed on Nov. 2, 2004. Further, this application is a continuation-in-part of U.S. patent application Ser. No. 10/408,665, filed on Apr. 8, 2003, now U.S. Pat. No. 7,162,303, which claims the benefit of U.S. Provisional Patent Application Nos. 60/442,970, filed on Jan. 29, 2003; 60/415,575, filed on Oct. 3, 2002; and 60/370,190, filed on Apr. 8, 2002.

(b) U.S. patent application Ser. No. 11/189,563, filed on Jul. 25, 2005.

(c) U.S. patent application Ser. No. 11/266,993, filed on Nov. 4, 2005, now U.S. Pat. No. 7,756,583.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. More particularly, the present invention relates to methods and apparatus for achieving pulsed electric field neuromodulation via an intra-to-extravascular approach.

BACKGROUND

Congestive Heart Failure ("CHF") is a condition that occurs when the heart becomes damaged and reduces blood flow to the organs of the body. If blood flow decreases sufficiently, kidney function becomes impaired, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to vasoconstriction of blood vessels supplying the kidneys, decreased renal blood flow, decreased removal of water and sodium from the body, and increased renin secretion. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, co-pending U.S. patent application Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

In some patients, when a PEF sufficient to initiate irreversible electroporation is applied to renal nerves and/or other neural fibers that contribute to renal neural functions, applicants believe that denervation induced by the PEF would result in increased urine output, decreased plasma renin levels, decreased tissue (e.g., kidney) and/or urine catecholamines (e.g., norepinephrine), increased urinary sodium excretion, and/or controlled blood pressure that would prevent or treat CHF, hypertension, renal system diseases, and other renal or cardio-renal anomalies. PEF systems could be used to modulate efferent or afferent nerve signals, as well as combinations of efferent and afferent nerve signals.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

Regardless of whether or not monitoring techniques are utilized, the applied energy or voltage from an intravascular PEF system necessary to establish an electric field of sufficient magnitude in the vicinity of target neural fibers in order to modulate the target neural fibers may be of a magnitude that causes persistent damage to non-target tissue, such as smooth muscle cells of the vessel wall. Thus, a desired treatment outcome, e.g., renal denervation, may not be achievable with some intravascular PEF systems in certain patients without concomitantly inducing persistent damage to the non-target tissue. It therefore would be desirable to provide methods and apparatus for reducing the required magnitude of applied energy or voltage necessary to achieve desired neuromodulation in target tissue and/or to increase localization of the sufficient magnitude induced electric field to the vicinity of the target tissue.

SUMMARY

The present invention provides methods and apparatus for pulsed electric field ("PEF") neuromodulation via an intra-to-extravascular ("ITEV") approach, e.g., to effectuate irreversible electroporation or electrofusion, necrosis and/or inducement of apoptosis, alteration of gene expression, changes in cytokine upregulation, and other conditions in target neural fibers. In some embodiments, the ITEV PEF system comprises an intravascular catheter having one or more electrodes configured for intra-to-extravascular placement across a wall of a patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

Pulsed electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. For example, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

The present invention relates to methods and apparatus for neuromodulation, e.g., denervation. More particularly, the present invention relates to methods and apparatus for achieving pulsed electric field neuromodulation via an intravascular-to-extravascular approach. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation is reduced relative to an intravascular PEF system having one or more electrodes positioned solely intravascularly. The methods and apparatus of the present invention may, for example, be used to modulate one or more target neural fibers that contribute to renal function.

The methods and apparatus of the present invention may be used to modulate a neural fiber that contributes to renal function and may exploit any suitable electrical signal or field parameters, e.g., any electric field that will achieve the desired neuromodulation (e.g., electroporative effect). To better understand the structures of devices of the present invention and the methods of using such devices for renal neuromodulation and monitoring, it is instructive to examine the renal anatomy in humans.

B. Selected Embodiments of Methods for Neuromodulation

Figure 1:
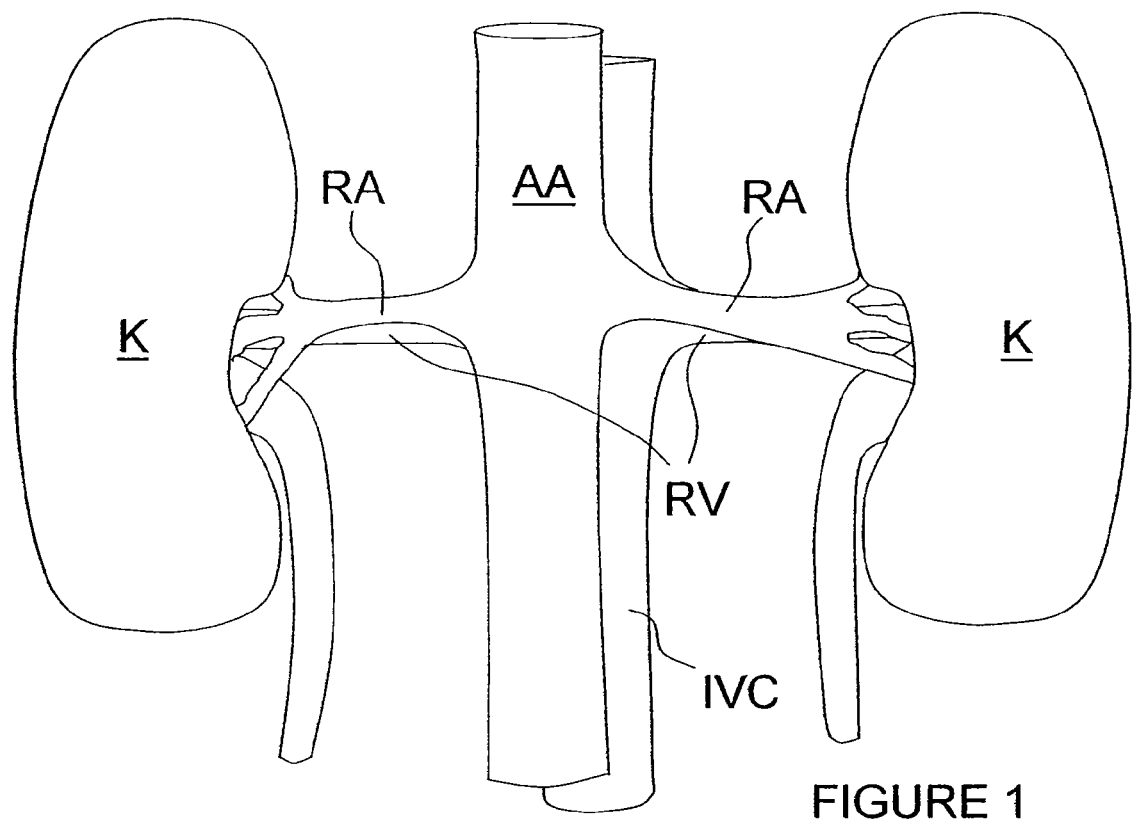
FIG. 1 is a schematic view illustrating human renal anatomy.
Figure 2:
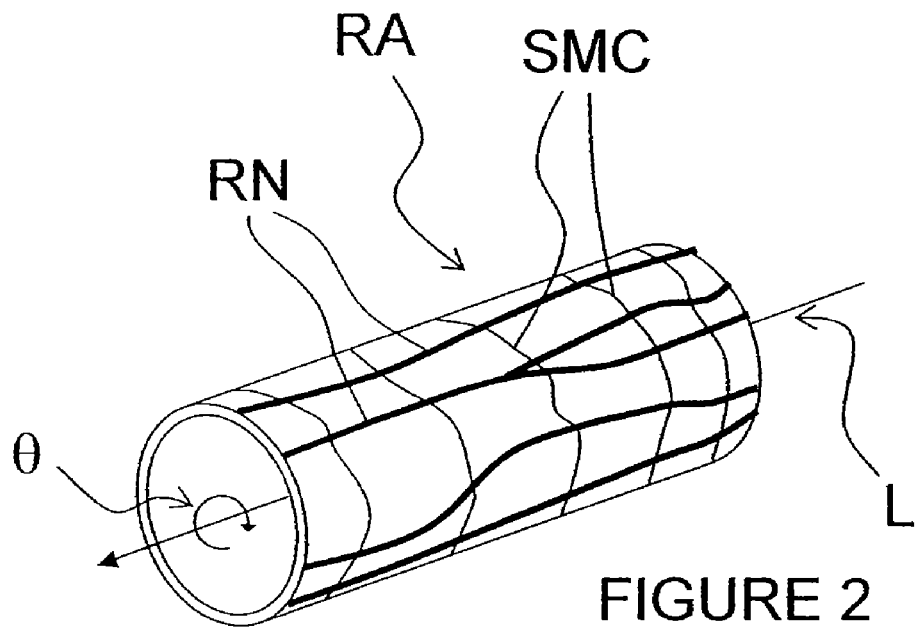
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
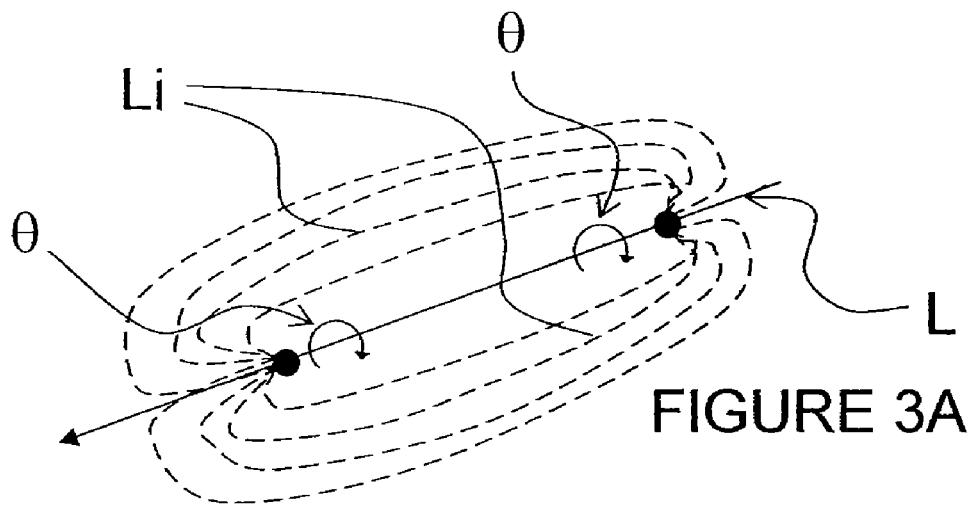
FIGS. 3A and 3B are schematic side- and end-views, respectively, illustrating orienting of an electric field for selectively affecting renal nerves.
Figure 3B:
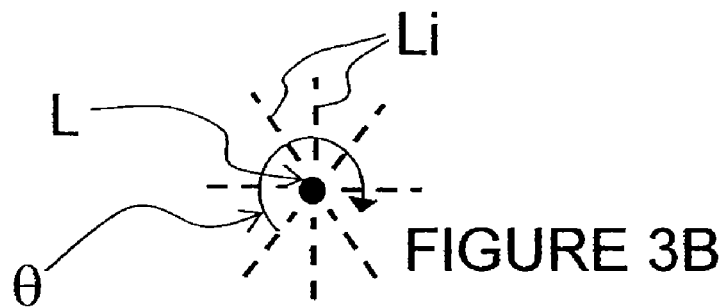

Referring to FIG. 3, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to change cytokine upregulation, and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or at least partially across the wall of the renal artery, e.g., via an intra-to-extravascular ("ITEV") approach, may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

C. Exemplary Embodiments of Systems and Additional Methods for Neuromodulation

With reference to FIG. 4, embodiments of intra-to-extravascular ("ITEV") PEF systems and methods of the present invention are described. ITEV PEF systems of the present invention are configured for temporary intravascular placement and for passage of one or more electrodes across a wall of the vasculature for extravascular placement. Furthermore, the systems are configured to deliver pulsed electric fields to neural fibers for neuromodulation. In one particular example, the systems are configured to deliver the pulsed electric fields to neural fibers that contribute to renal function in order to achieve renal neuromodulation. For the purposes of the present invention, extravascular shall refer to any position external to the intima and media layers of the vasculature. Extravascular may, for example, include positions within the adventitia of the vessel or within surrounding fatty tissue.

In FIGS. 4A-D, an ITEV PEF system 100 comprises an intravascular catheter 102 having a lumen 103, a shaped cannula 104 configured for low-profile delivery within the lumen 103 and for advancement from the lumen 103 in order to pierce the wall of a patient's vasculature, and a first guide wire electrode 106 configured for advancement through a lumen 105 of the cannula 104. The cannula 104 may, for example, be fabricated from a shape memory material (e.g., Nitinol) or a flexible, pre-formed elastic material (e.g., thin-walled stainless steel).

Figure 4A:
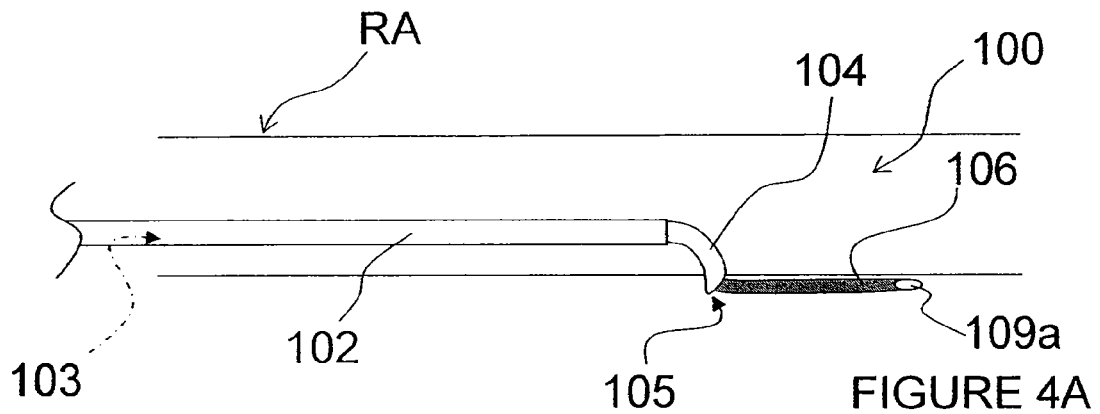
FIGS. 4A-4D are schematic side-views, partially in section, illustrating methods and apparatus for pulsed electric field neuromodulation via an intra-to-extravascular approach having a bipolar electrode pair with at least one of the electrodes of the pair positioned extravascularly.
Figure 4B:
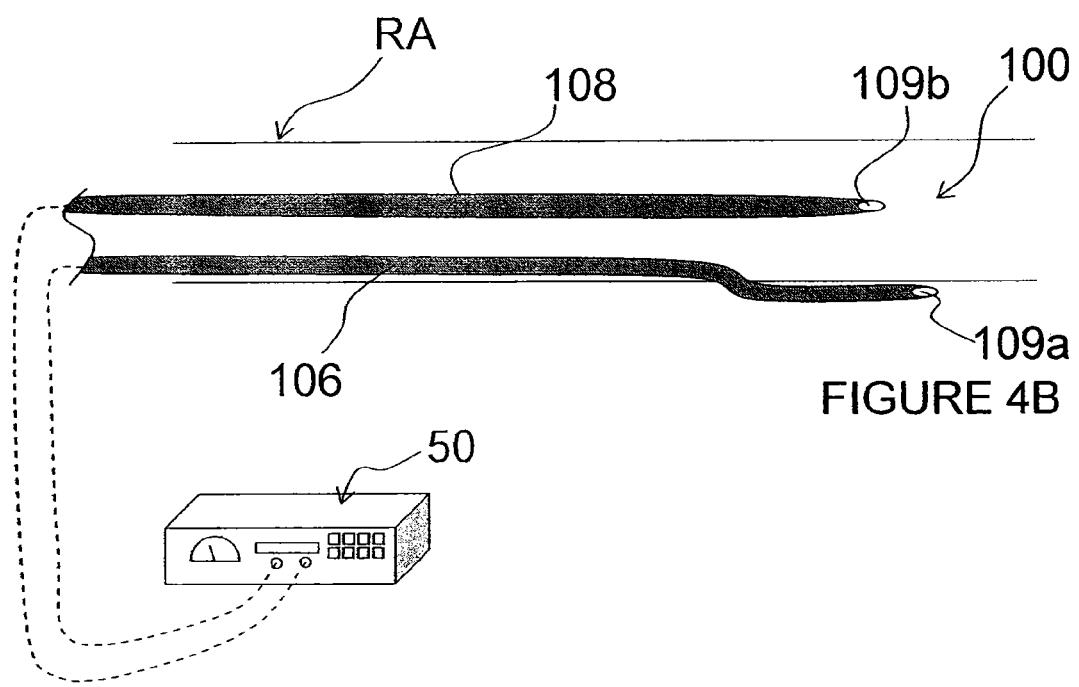

In the embodiment of FIGS. 4A and 4B, system 100 further comprises a second guide wire electrode 108 (FIG. 4B) configured for intravascular positioning. The guide wire electrodes 106 and 108, which form a bipolar electrode pair, optionally may be insulated at all regions, except their distal ends. The electrodes are electrically connected to a pulsed electric field generator 50 (FIG. 4B) located external to the patient. The generator may be utilized with any embodiment of the present invention to deliver a PEF with desired field parameters. It should be understood that several examples of PEF-delivery electrodes described below may be electrically connected to the generator even though the generator is not explicitly shown or described with each embodiment.

In use, the catheter 102 may be delivered to renal artery RA as shown in FIG. 4A, or it may be delivered through a guide catheter or other device to a renal vein or to any other vessel in proximity to target neural tissue (e.g., target neural tissue that contributes to renal function). The catheter preferably is delivered via a percutaneous technique, such as via a percutaneous femoral artery access. Once the shaped cannula 104 is positioned within the patient's vasculature, it may be advanced past the outlet of the lumen 103 of the catheter 102 such that the cannula 104 assumes a curved or otherwise angular profile. As the cannula 104 advances further, it pierces the wall of the patient's vasculature to be positioned extravascularly (i.e., at least within the adventitia). The first guide wire electrode 106 is then advanced through the cannula lumen 105 such that a non-insulated distal region 109a of the first electrode 106 is positioned extravascularly via an intra-to-extravascular approach. The cannula 104 may be retracted, and the catheter 102, as well as the cannula 104 may be removed from the patient or from the treatment site. The second guide wire electrode 108 has a non-insulated distal region 109b that is positioned intravascularly (before, during or after extravascular placement of the first electrode 106) to form a bipolar electrode pair with the first electrode 106 (FIG. 4B).

The first electrode 106 preferably comprises the active electrode and the second electrode 108 preferably comprises the return electrode. However, it should be understood that the electrode polarities optionally may be reversed. The non-insulated distal regions 109a-b of the electrodes 106 and 108 optionally may be in substantial alignment along a cross-sectional plane through renal artery RA. Alternatively, the distal regions 109a-b may be spaced apart longitudinally. Such longitudinal spacing of the distal regions 109a-b may, for example, better align a pulsed electric field delivered across the electrodes with a longitudinal dimension of the renal artery to facilitate modulation of renal nerves with limited effect on non-target smooth muscle cells or other cells, as described previously with respect to FIG. 3.

With the first and second electrodes 106 and 108 positioned as desired, a pulsed electric field generated by the PEF generator 50 is transmitted through the electrodes 106 and 108 and delivered across the non-insulated distal regions 109a-b of the electrodes. The PEF therapy modulates activity along neural fibers that directly or indirectly contribute to renal function (e.g., denervates neural fibers related to renal function). This may be achieved, for example, via irreversible electroporation, electrofusion, necrosis and/or inducement of apoptosis in the nerve cells, alteration of gene expression, changes in cytokine upregulation, and/or other suitable processes. After delivery of PEF therapy, the ITEV PEF system 100 may be removed from the patient to conclude the procedure.

It is expected that PEF therapy using the ITEV PEF system 100 will alleviate clinical symptoms of CHF, hypertension, renal disease and/or other cardio-renal diseases for a period of months, potentially up to six months or more. This time period might be sufficient to allow the body to heal; for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

In order to denervate or otherwise modulate target neural fibers, the ITEV PEF system 100 should generate an electric field of sufficient strength or magnitude across the fibers to induce such denervation or modulation. When utilizing an intravascular PEF system, depending upon the arrangement and positioning of the PEF electrodes, as well as the physiology of the patient, the applied voltage necessary to achieve a field strength of sufficient magnitude at the target neural fibers also may be of sufficient magnitude to induce undesirable persistent injury in non-target tissue, such as smooth muscle cells and/or the vessel wall. It is expected that the extravascular positioning of electrode 106 via an intra-to-extravascular approach will reduce the necessary applied voltage for denervation or modulation (e.g., renal denervation or modulation) via PEF therapy compared to the applied voltage required when utilizing solely intravascular apparatus with similarly spaced and sized electrodes. Specifically, extravascular placement of electrode 106 in closer proximity to the target neural fibers is expected to increase localization of the peak induced electric field to the vicinity of the target neural fibers.

Figure 4C:
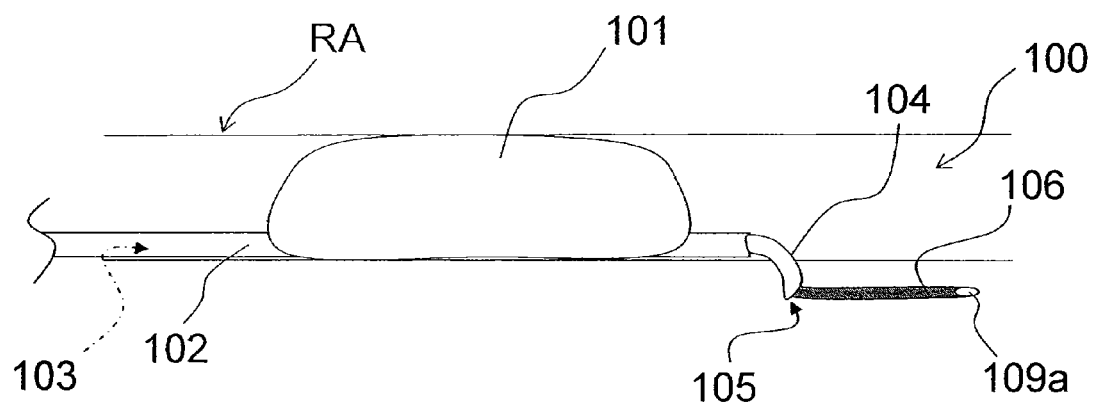
Figure 4D:
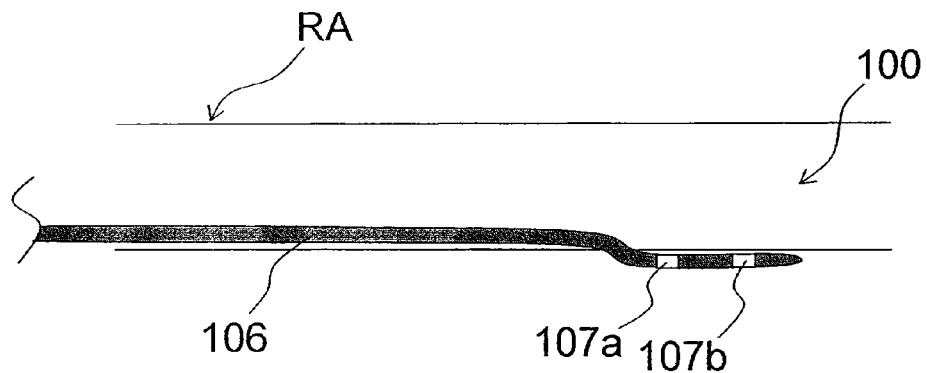

As seen in FIG. 4C, the catheter 102 optionally may comprise an expandable element 101 (e.g., an inflatable balloon) that stabilizes the catheter 102 within the patients vessel. The expandable element 101 further facilitates piercing of the vessel wall with the cannula 104 to position the first electrode 106 at an extravascular location. As seen in FIG. 4D, the first electrode 106 may comprise a spaced bipolar electrode pair 107a and 107b to obviate the need for the intravascular second electrode 108. The PEF therapy may be delivered extravascularly across the bipolar electrode pair 107a-b.

The extravascular second electrode 106 optionally may be replaced with a virtual electrode. For example, conductive saline may be injected through cannula 104 into the extravascular space. The conductive saline may provide a virtual electrode surrounding all or part of the circumference of the vessel and may be used in a bipolar fashion with intravascular electrode 108.

Figure 5:
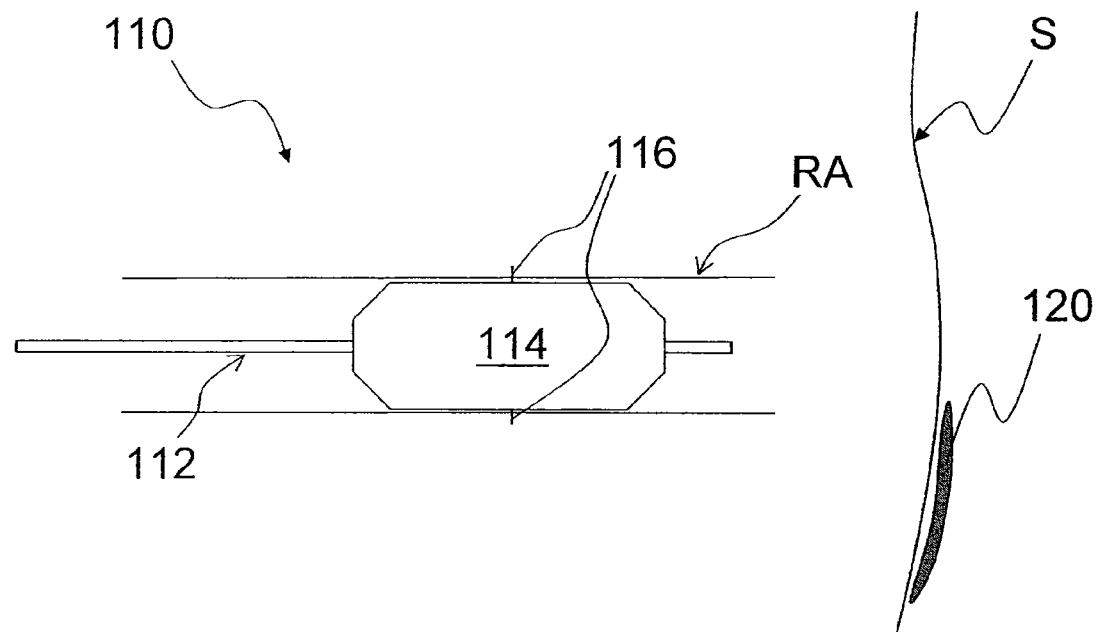
FIG. 5 is a schematic view, partially in section, illustrating methods and apparatus for monopolar pulsed electric field neuromodulation via an intra-to-extravascular approach.

The examples of the ITEV PEF systems of FIGS. 4A-D optionally may be utilized in a monopolar fashion by replacing the intravascular second electrode 108 with a ground pad coupled to the PEF generator 50 and attached to the exterior of the patient. FIG. 5 illustrates an alternative monopolar ITEV PEF system 110 comprising a catheter 112 having an expandable element 114 with one or more needle-like ITEV electrodes 116 coupled to the expandable element. When multiple needle electrodes 116 are provided, they may be spaced circumferentially and/or longitudinally about/along the expandable element 114. The system 110 further comprises a ground pad 120 attached to the skin S of the patient along the exterior of the patient (e.g., to the patient's flank, back or thigh) and coupled to the PEF generator 50 as a return electrode. The ground pad 120 optionally may be positioned directly lateral to the ITEV electrode(s) 116 to direct the PEF therapy along the patient's vasculature (e.g., along renal artery RA).

The expandable element 114 comprises a member or structure configured for intravascular delivery to (and retrieval from) a target location in a low profile configuration and for expansion to an expanded deployed configuration at the target location. The expandable element 114 may comprise, for example, an inflatable balloon, an expandable basket or cage, or other expandable structure. As seen in FIG. 5, expansion of the expansion element 114 causes the ITEV electrode(s) 116 to pierce the wall of renal artery RA and move from an intravascular location to an extravascular location. With the ITEV electrode(s) 116 positioned extravascularly and coupled to the PEF generator 50, the ITEV electrode(s) may be energized as active electrodes in a monopolar PEF therapy with the external ground pad 120 serving as the return electrode.

Figure 6A:
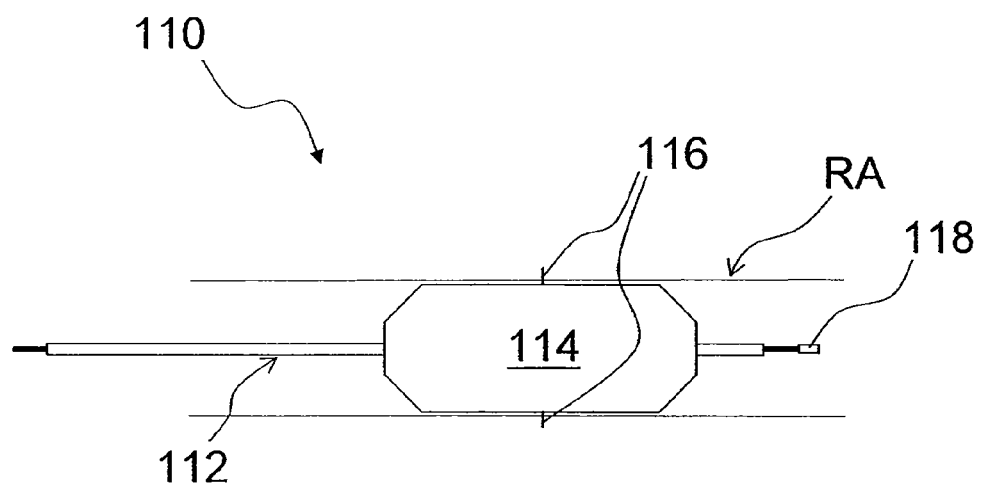
FIGS. 6A-6C are schematic side-views, partially in section, illustrating alternative embodiments of the methods and apparatus of FIG. 5, the methods and apparatus comprising a bipolar electrode pair having a first electrode positioned extravascularly and a second electrode positioned intravascularly.
Figure 6B:
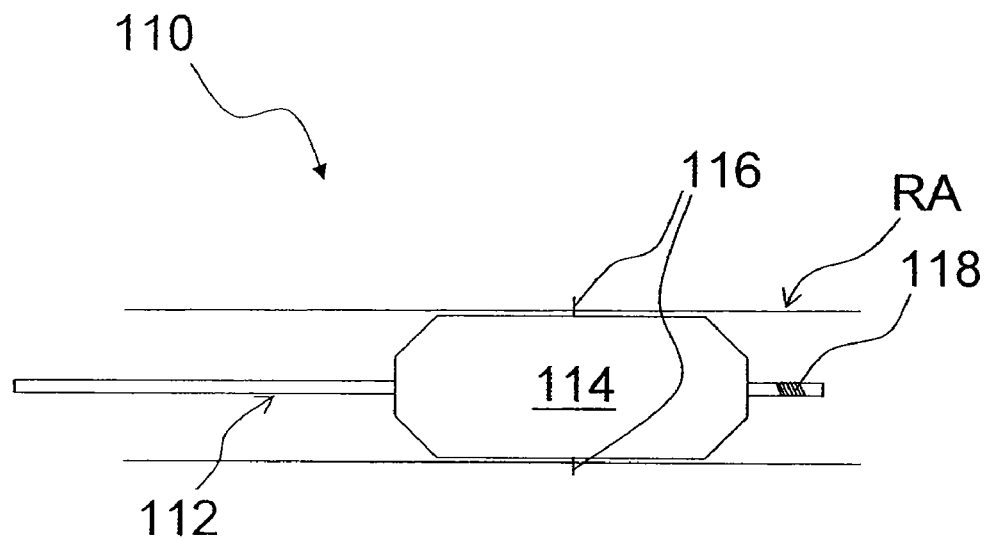
Figure 6C:
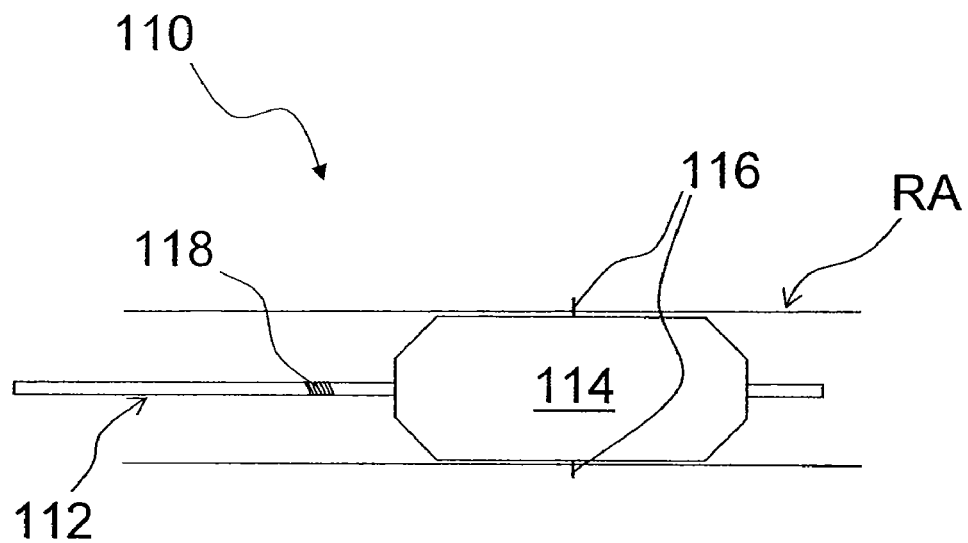

Referring now to FIGS. 6A-C, alternative embodiments of the ITEV PEF system 110 are described comprising a first electrode positioned extravascularly and a second electrode positioned intravascularly. In FIGS. 6A-C, the ITEV PEF systems 110 again comprise the catheter 112 having the expandable element 114 with one or more ITEV electrodes 116 coupled to the expandable element and configured for intra-to-extravascular delivery. The systems 110 further comprise an intravascular second electrode 118 positioned within the vessel. In FIG. 6A, the second electrode 118 comprises a guidewire electrode positioned within the lumen of the catheter 112. The guidewire electrode 118 is coupled to the PEF generator 50 and is insulated at regions other than a distal region positioned distal of the catheter 112. In FIG. 6B, the second electrode 118 is coupled to the shaft of the catheter 112 distally of the expandable element 114. In FIG. 6C, the second electrode 118 is coupled to the shaft of catheter 112 proximally of the expandable element 114. In use, the ITEV electrode(s) 116 may comprise active electrode(s) and the second electrode 118 may comprise a return electrode, or vice versa. The second electrode 118 optionally may be longitudinally spaced relative to the ITEV electrode(s) 116 to align the PEF therapy with a longitudinal axis of the patient's vasculature, as described previously with respect to FIGS. 2 and 3. The second electrodes 118 may, for example, be fabricated from wound coils of wire. When utilizing relatively long electrodes, wound coils allow the catheter 112 to maintain desired flexibility.

Figure 7A:
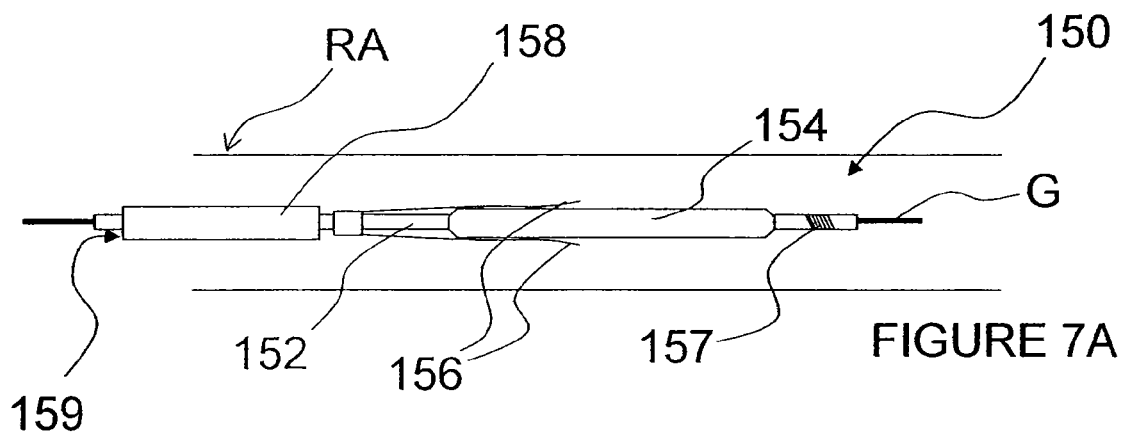
FIGS. 7A and 7B are schematic side-views, partially in section, illustrating additional methods and apparatus for pulsed electric field neuromodulation via a bipolar electrode pair, the bipolar electrode pair comprising at least one first electrode positioned extravascularly and at least one second electrode positioned intravascularly.
Figure 7B:
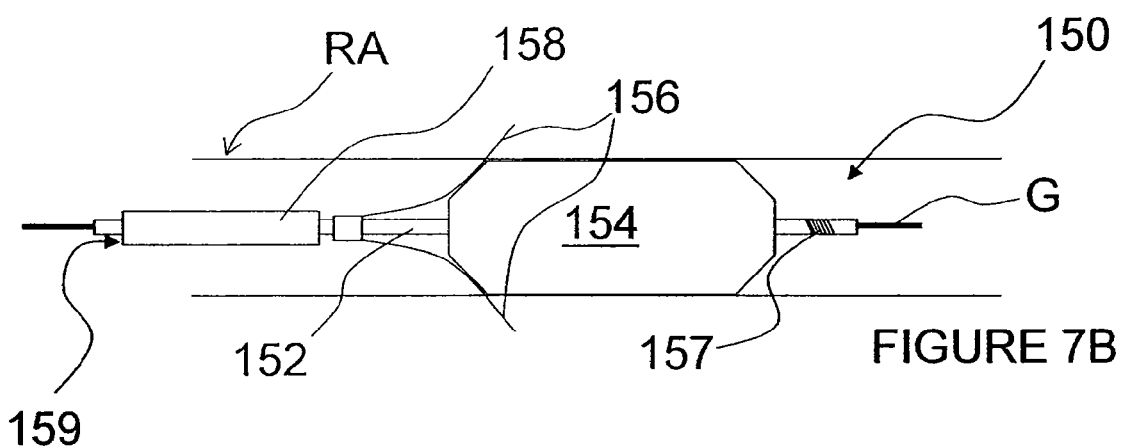

Referring now to FIGS. 7A and 7B, additional methods and apparatus for pulsed electric field neuromodulation via a bipolar electrode pair having a first electrode positioned extravascularly and a second electrode positioned intravascularly are described. FIGS. 7A and 7B, more specifically, illustrate an ITEV PEF system 150 comprising a catheter 152 and an expandable element 154, which may comprise an inflatable balloon or an expandable wire cage. The system 150 further comprises one or more ITEV needle electrodes 156 that are coupled to the catheter 152, illustratively proximal of expandable element 154, and return electrode 157, illustratively coupled to the shaft of catheter 152 distal of expandable element 154. Additionally, the system comprises a protective sheath 158 having a lumen 159 in which the catheter 152 may be positioned for percutaneous advancement and/or retrieval.

In FIGS. 7A and 7B, the distal regions of the ITEV electrodes 156 extend laterally over, but are not connected to, at least a portion of the expandable element 154. This is in contrast to the previously described ITEV PEF systems of FIGS. 4-6 that have ITEV electrodes coupled directly to an expandable element. By separating the ITEV electrode(s) 156 from the expandable element 154, the system 150 of FIGS. 7A and 7B may simplify manufacturing and/or enhance expansion reliability.

As seen in FIG. 7A, the catheter 152 and the protective sheath 158 may be advanced into position within the patient's vasculature (e.g., within renal artery RA over guidewire G). Once in position, the sheath 158 may be retracted relative to the catheter 152 and/or the catheter 152 may be advanced relative to the sheath 158 such that the expandable element 154, the ITEV electrode(s) 156 and the return electrode 157 are positioned distally of the protective sheath 158. As seen in FIG. 7B, the expandable element 154 then may be expanded, such that the ITEV needle electrode(s) 156 puncture the vessel wall and are positioned extravascularly via an ITEV approach. Once the electrode(s) 156 are positioned extravascularly, PEF therapy may proceed between the ITEV electrode(s) 156 and the return electrode 157. The PEF therapy, for example, can modulate and/or denervate a neural fiber that contributes to renal function. Upon completion of the PEF therapy, the expandable element 154 may be collapsed, and the sheath 158 may be advanced relative to the catheter 152, such that the ITEV electrodes 156 are removed from the vessel wall. The system 150 then may be removed from the patient to complete the procedure.

Figure 8A:
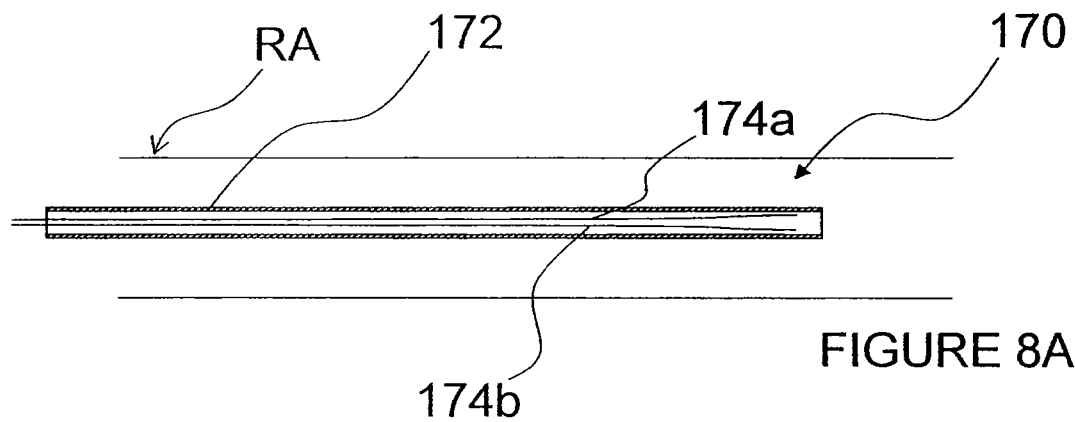
FIGS. 8A-8C are a schematic side-sectional view and schematic side-views, partially in section, illustrating methods and apparatus for pulsed electric field neuromodulation having at least one bipolar electrode pair with both electrodes of each electrode pair positioned extravascularly via an intra-to-extravascular approach.
Figure 8B:
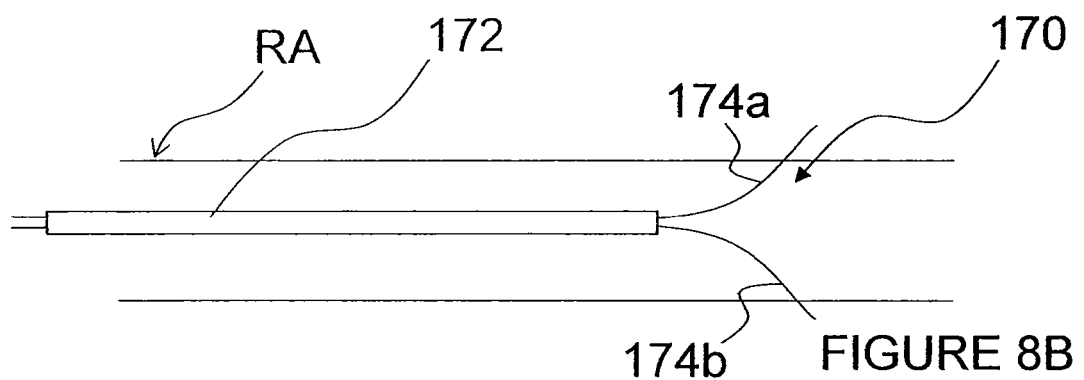
Figure 8C:
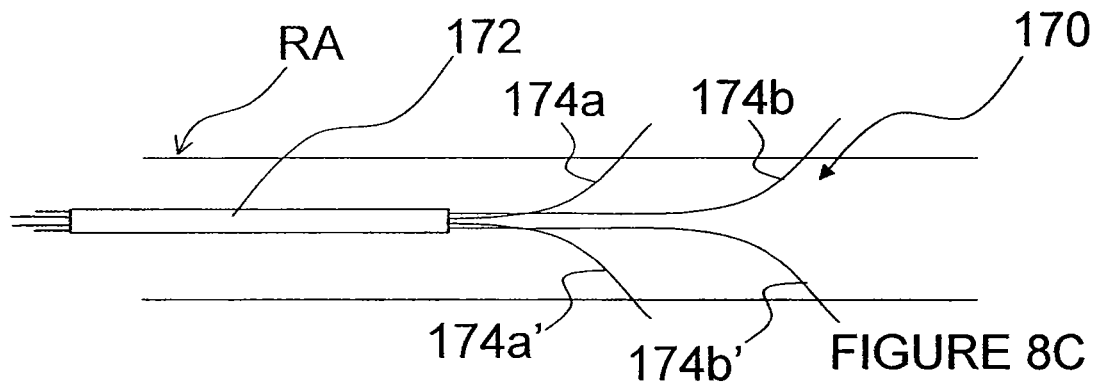

Referring now to FIGS. 8A-C, methods and apparatus for pulsed electric field neuromodulation are described utilizing one or more bipolar electrode pairs with both electrodes of each pair positioned extravascularly via an intra-to-extravascular approach. One example of such an ITEV PEF system 170 comprises a catheter or sheath 172 having shaped ITEV bipolar needle electrodes 174a and 174b that are configured for advancement to an intravascular location within the sheath. The electrodes 174a-b may have shape-memory properties (e.g., may be fabricated from a shape-memory alloy such as Nitinol) and may be insulated at locations other than their distal regions. As seen in FIG. 8B, upon advancement of the electrodes 174a-b to a position distal of the sheath 172 (e.g., via retraction of the sheath), the electrodes 174a-b assume their preformed shape and puncture the wall of the patient's vasculature, illustratively renal artery RA, such that the distal regions of the electrodes 174a-b are positioned extravascularly via an ITEV approach. As will be apparent, electrodes 174a and 174b may be longitudinally spaced relative to one another to better align the PEF therapy with a longitudinal dimension of the patient's vasculature. Furthermore, although the electrodes illustratively are spaced radially about 180° apart, it should be understood that the electrodes alternatively may be spaced with any desired radial separation (or lack thereof).

FIG. 8C illustrates another example of the ITEV PEF system 170 comprising multiple pairs of ITEV electrodes that are longitudinally spaced. The system 170, for example, can comprise a first bipolar electrode pair 174a and 174b, and a second bipolar electrode pair 174a' and 174b'. Additional pairs of bipolar electrodes at different circumferential positions or with different longitudinal spacing may be utilized as desired in other examples.

Once properly positioned, PEF therapy may be delivered across the electrodes 174 to achieve desired neuromodulation. Upon completion of the PEF therapy, the needle electrodes 174 may be retracted relative to the sheath 172, and/or the sheath 172 may be advanced relative to the electrodes 174, such that the electrodes are removed from the wall of the patient's vasculature and coaxed back into a constrained retrieval configuration within the sheath. The ITEV PEF system 170 then may be removed from the patient to complete the procedure.

Figure 9:
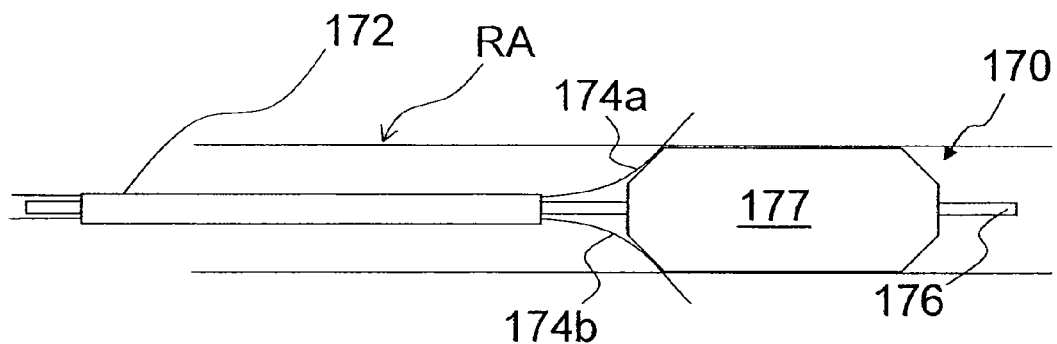
FIG. 9 is a schematic side-view, partially in section, of an alternative embodiment of the apparatus and methods of FIG. 8.

With reference to FIG. 9, an alternative embodiment of the ITEV PEF system 170 is described comprising a catheter 176 having an expandable element 177. The expandable element 177 acts as a guide that, when expanded, directs or forces the electrodes 174 across the vessel wall. More specifically, the expandable element 177 can direct the electrodes 174 through the vessel wall by advancing the electrodes 174 along the expandable element 177 after it has been expanded. Alternatively, the expandable element 177 can force the electrodes 174 across the vessel wall by advancing the electrodes 174 over the expandable element 177 while the expandable element 177 is in a reduced profile configuration and then expanding of the expandable element 177 to force the electrodes 174 across the wall of the vessel.

Figure 10A:
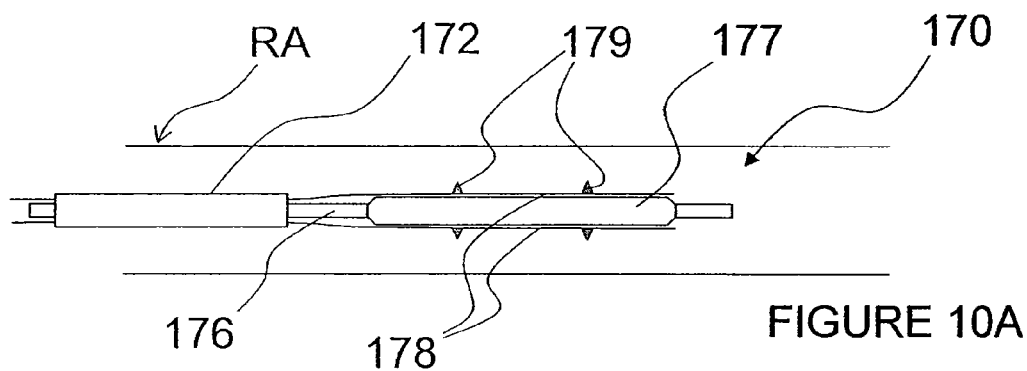
FIGS. 10A-10F are schematic side-views, partially in section, of alternative embodiments of the apparatus and methods of FIG. 9 comprising multiple pairs of bipolar electrodes.
Figure 10B:
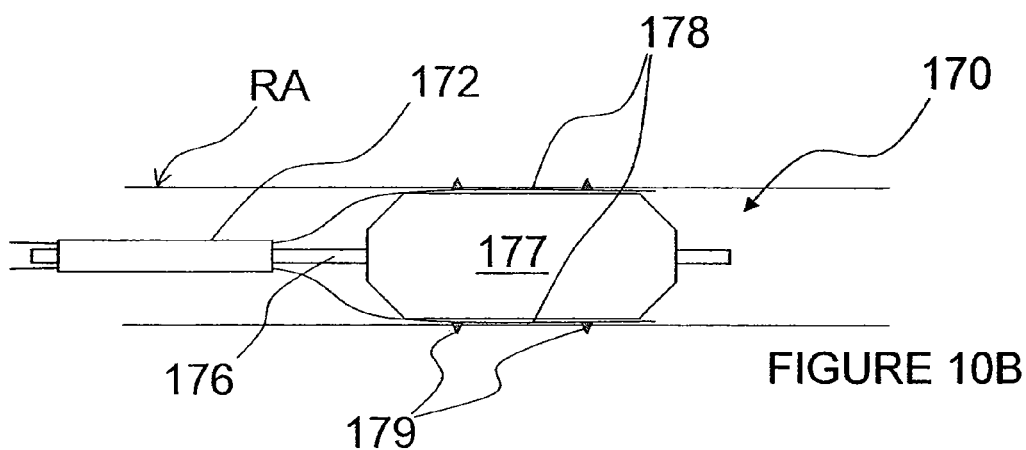

FIGS. 10A-F illustrate additional alternative embodiments of the ITEV PEF system 170 comprising multiple pairs of bipolar electrodes. In FIGS. 10A and 10B, the ITEV electrodes 174 have been replaced with ITEV electrode carriers 178. Each ITEV electrode carrier 178 comprises multiple electrodes 179. For example, each electrode carrier 178 may comprise a pair of electrically-isolated bipolar electrodes 179. Alternatively, each carrier 178 may comprise multiple electrodes 179 of a common polarity. The electrodes 179 comprise sharpened points, pins, or other raised features for penetrating the wall of the patient's vasculature. As seen in FIG. 10A, the electrodes 179 may be delivered to the stimulation site in a low profile configuration, e.g., through or within the sheath 172. The electrodes 179 then may be positioned extravascularly via an ITEV approach by expanding the expandable element 177, as in FIG. 10B.

Figure 10C:
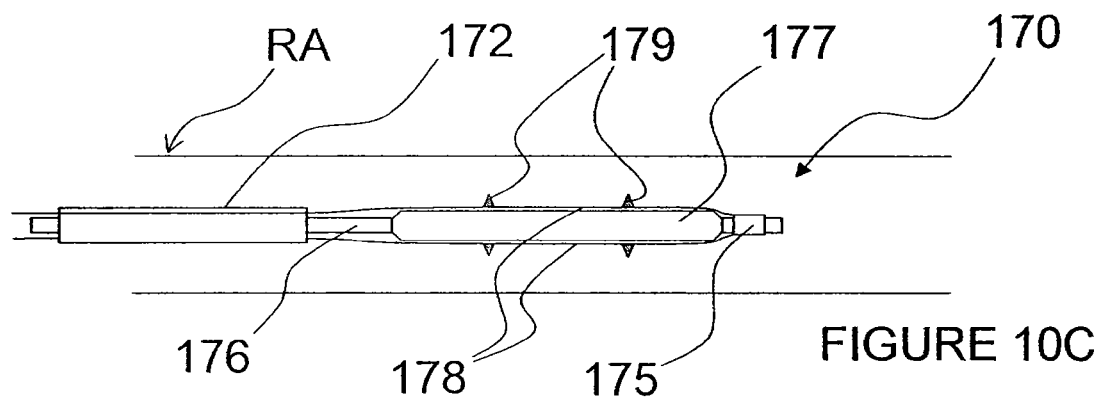
Figure 10D:
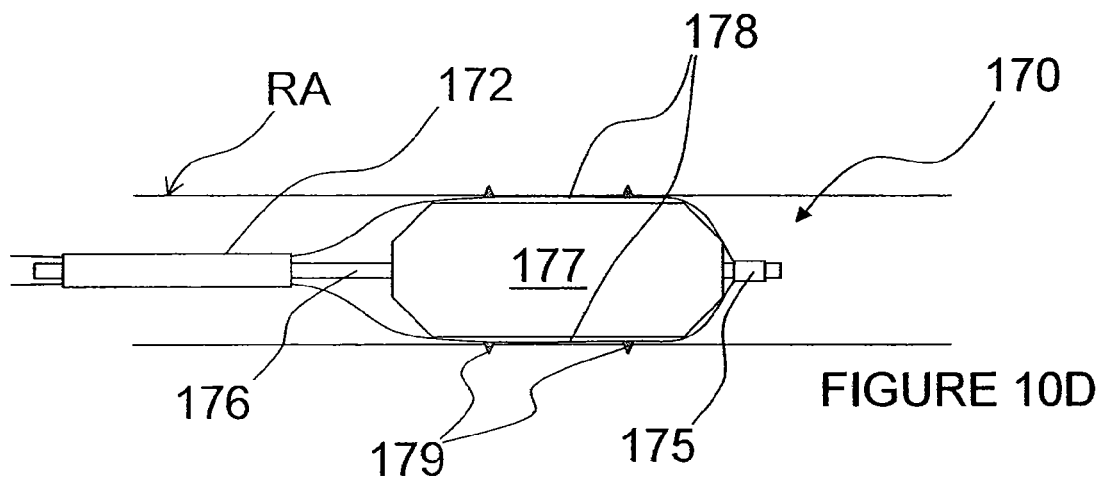

As seen in FIGS. 10C and 10D, the electrode carriers 178 optionally may be coupled to a catheter 176 distal of the expandable element 177 at a collar 175. The collar 175 may be slidingly attached to the catheter 176 and/or may be longitudinally constrained. An expected benefit of attaching the carriers to the catheter is good control of the extravascular positioning of electrodes 179 via an ITEV approach.

Figure 10E:
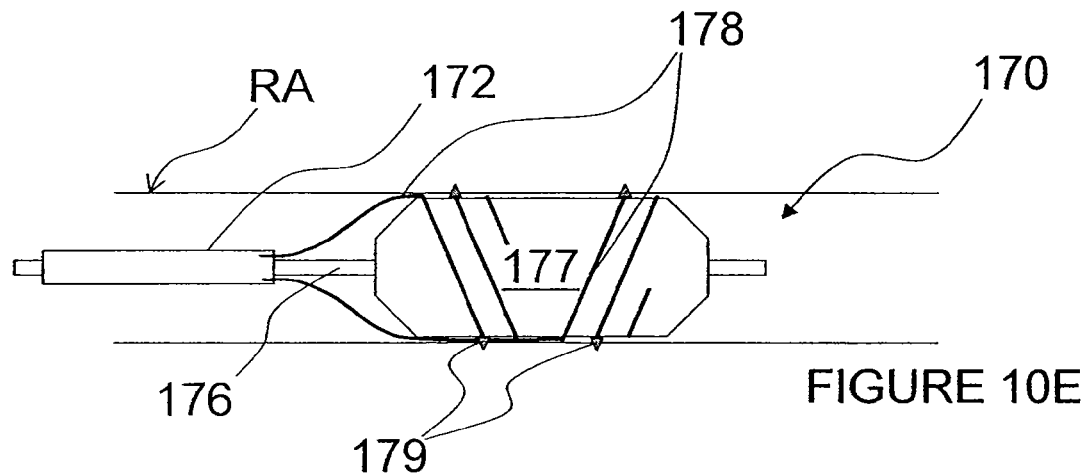

As seen in FIG. 10E, the electrode carriers 178 optionally may spiral around the expandable element 177. The carriers 178 optionally may comprise several electrodes 179 positioned at multiple circumferential positions to facilitate more circumferential PEF therapy. The electrode carriers 178 preferably are electrically isolated from one another. For example, the carriers 178 may be insulated at all regions except for at the electrodes 179.

Figure 10F:
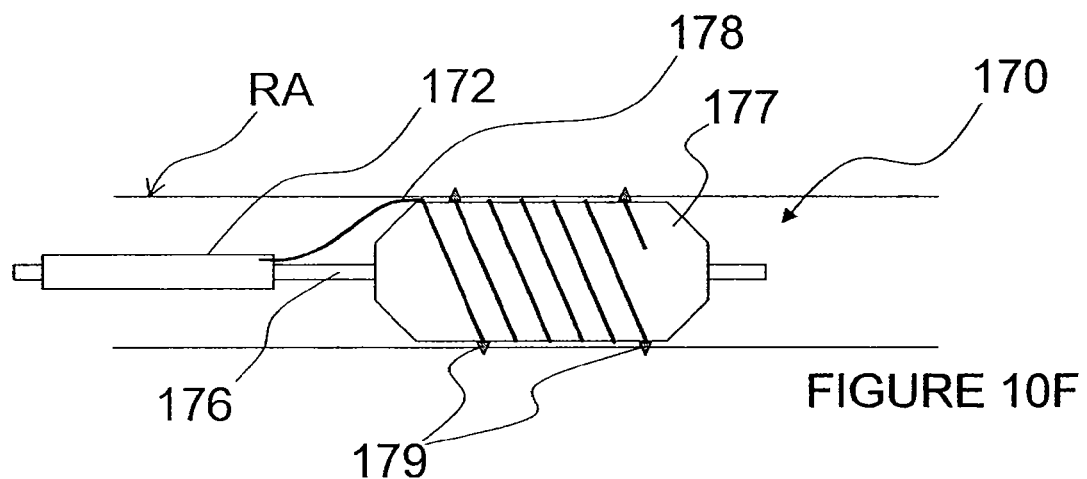

As seen in FIG. 10F, the system 170 optionally may comprise a single electrode carrier 178 that spirals around the expandable element 177. A plurality of the electrodes along the unitary carrier may be of a common polarity and/or may be electrically isolated from one another and of varying polarity to form bipolar electrode pair(s). The electrodes 179 may be positioned a multiple circumferential positions, as desired.

Figure 11A:
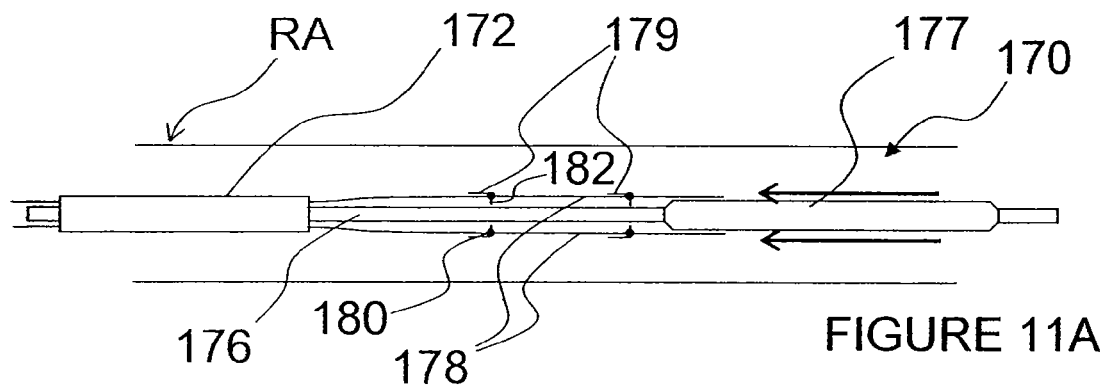
FIGS. 11A-11C are schematic side-views, partially in section, of an alternative embodiment of the apparatus and methods of FIG. 10 comprising a safety feature for intravascular delivery of the electrodes prior to extravascular placement.
Figure 11B:
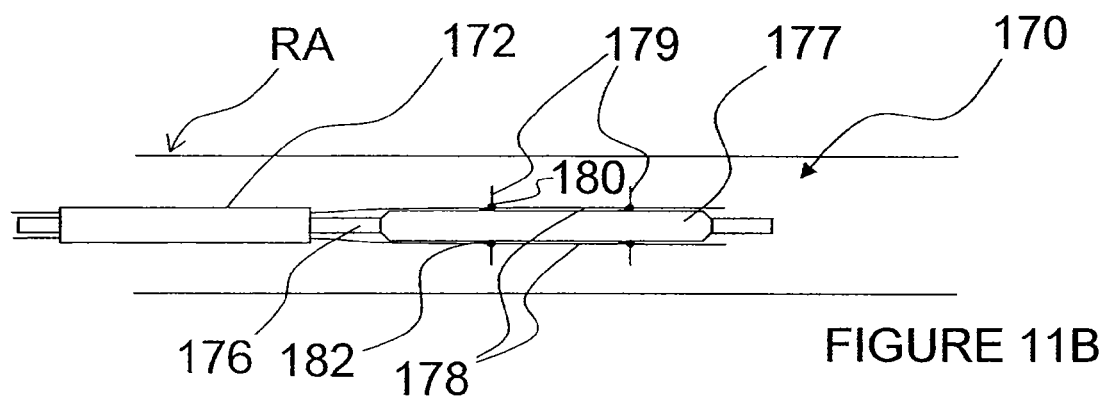
Figure 11C:
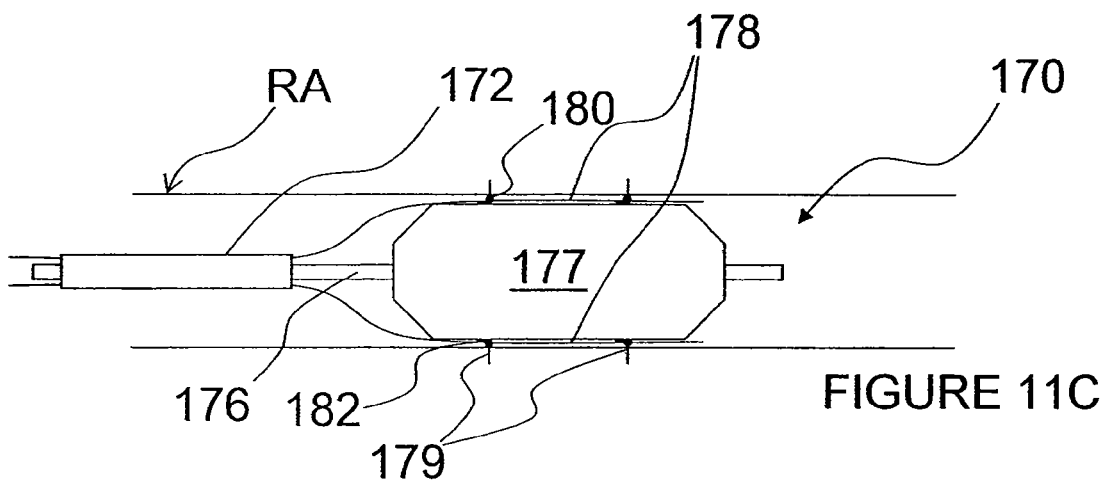

FIGS. 11A-C show additional examples of the ITEV PEF system 170 comprising a safety feature that facilitates intravascular delivery of the electrodes 179 prior to extravascular placement of the electrodes. In the embodiment of FIGS. 11A-C, the electrodes 179 are coupled to electrode carriers 178 in a manner that facilitates rotation of the electrodes 179 relative to the respective carriers 178. For example, the electrodes 179 may be coupled to the carriers 178 at pivots 180, which may comprise rotational bearing surfaces. Furthermore, the electrodes 179 comprise extensions 182 that co-act with the expandable element 177 to selectively rotate the electrodes 179 between a reduced delivery and retrieval profile and an expanded profile suitable for ITEV delivery of the electrodes. The electrodes 179 optionally may be biased towards the reduced profile, e.g., via a spring mechanism. The reduced profile serves as a safety feature that reduces a risk of inadvertent perforation of vascular tissue prior to ITEV placement of the electrodes at a treatment site.

As seen in FIG. 11A, the electrodes 179 lie flat near or against the electrode carrier 178 during delivery to an intravascular treatment site (e.g., through or within the sheath 172). The electrodes 179 are positioned proximal of the expandable element 177 during delivery. Once positioned within the vessel, the electrodes 179 are expanded such that their tips point radially outward by retracting the expandable element 177 relative to the electrode carriers 178. As seen in FIG. 11B, retraction of the expandable element 177 causes it to engage the extensions 182 of the electrodes 179 such that the electrodes 179 rotate about the pivots 180 to the expanded configuration suitable for ITEV delivery of the electrodes 179. The expandable element 177 then is expanded, such that the electrodes 179 are forced through the vessel wall via an ITEV approach, as in FIG. 11C. ITEV PEF therapy then may proceed, as desired. Upon completion of the therapy, the expandable element 177 and the electrodes 179 are returned to the reduced profile configuration for retrieval from the patient.

Figure 12:
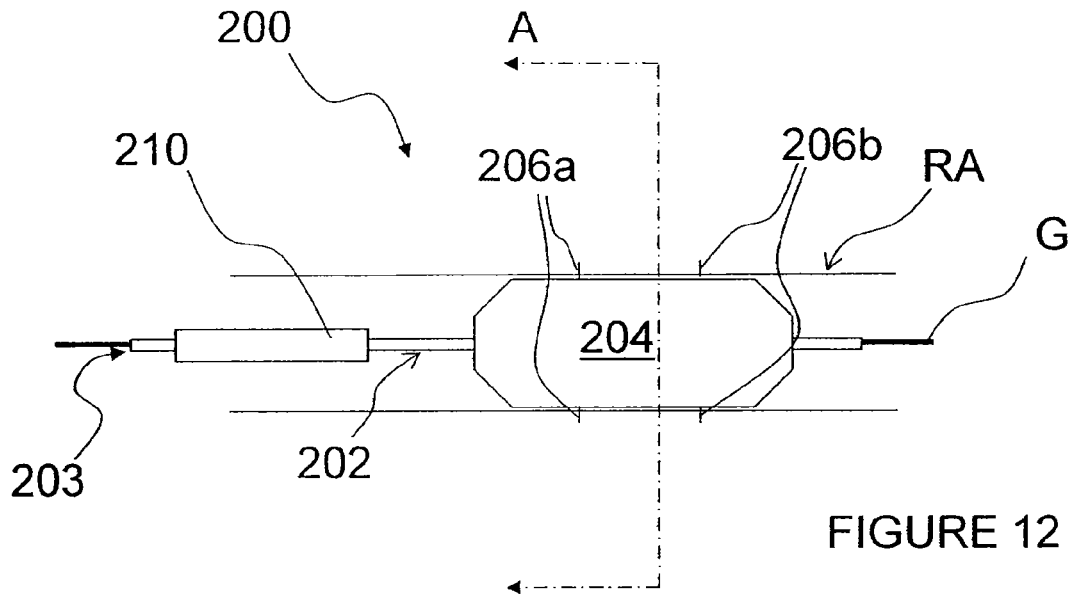
FIG. 12 is a schematic side-view, partially in section, of methods and apparatus for pulsed electric field neuromodulation via at least one angularly-aligned, longitudinally-spaced bipolar electrode pair positioned extravascularly via an intra-to-extravascular approach.

With reference now to FIG. 12, methods and apparatus for pulsed electric field neuromodulation via at least one angularly-aligned, longitudinally-spaced bipolar electrode pair positioned extravascularly via an intra-to-extravascular approach are described. FIG. 12, more specifically, shows an example of an ITEV PEF system 200 that comprises a catheter 202 having an expandable element 204 with at least one pair of longitudinally-spaced bipolar needle electrodes 206a and 206b. The needle electrodes 206a-b are positioned at substantially the same angular position along the expandable element (in FIG. 12, the system illustratively comprises two pairs of longitudinally-spaced, angularly-aligned bipolar electrodes 206a-b positioned at distinct circumferential positions). Angular alignment of the longitudinally-spaced bipolar electrodes 206a-b may align the PEF therapy with a longitudinal axis of target neural fibers, as described previously. The bipolar pairs of needle electrode 206 may comprise any desired longitudinal spacing; for example, the electrodes may comprise spacing in the range of about 0.5-10 mm.

The ITEV PEF system 200 may be delivered to an intravascular treatment site, such as a site within renal artery RA, using well-known percutaneous techniques. For example, the system 200 may be advanced over a guidewire G positioned with a lumen 203 of a catheter 202, which may be advanced through/within a guide catheter or a sheath 210. Once positioned at the treatment site, an expansion element 204 is expanded to force the bipolar needle electrodes 206 across the wall of the vessel such that the ends of the electrodes 206 are positioned extravascularly via an ITEV approach. The expansion element 204 may, for example, be expanded by (a) inflating a balloon, (b) self-expanding a basket or cage after positioning the element 204 distal of sheath 210, and/or (c) mechanical expanding a basket or cage via various push/pull and/or tension/compression techniques.

Positioning the electrodes 206 using an ITEV technique places the electrodes in closer proximity to target neural fibers that contribute to renal function. As discussed previously, renal nerves may be located in the adventitia of the renal arteries and/or in tissue immediately surrounding the renal arteries. Such ITEV positioning of the electrodes, as well as selected angular alignment of the bipolar electrode pair(s), may reduce energy requirements necessary to achieve desired neuromodulation, as compared to a PEF system comprising intravascularly-positioned electrodes.

The electrodes 206 preferably are of small enough caliber to safely cross the wall of renal artery RA without significant risk of bleeding, vessel wall injury, etc. For example, the electrodes may be of a caliber less than about 23 Gauge. Furthermore, the electrodes may be solid or may comprise one or more lumens. When with lumen(s), the needle electrodes may be configured for infusion of agents that either enhance the desired neuromodulatory effect (e.g., saline injection may be used to locally enhance conductivity during PEF therapy) or provide protective effects (e.g., cooling agents may be injected to protect non-target tissues).

The needle electrodes 206 also may be conductive along their entire lengths or may be insulated along at least part of their lengths. For example, the needle electrodes 206 can be insulated at locations other than their distal ends. Insulation along part of the lengths of electrodes 206 may reduce undesirable delivery of pulsed electric field therapy to non-target tissues, e.g., the intima or to the media of the patient's vessel. Such insulated electrodes preferably comprise lengths sufficient to place the non-insulated portions of the electrodes extravascularly at positions at least within the vasculature adventitia during ITEV positioning of the electrodes.

Figure 13A:
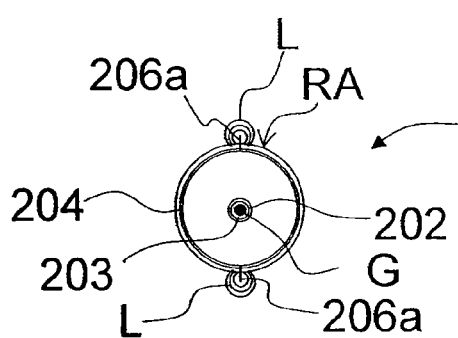
FIGS. 13A-13D are schematic cross-sectional views along section line A-A of FIG. 12, illustrating methods and apparatus for circumferential pulsed electric field modulation of target neural fibers via multiple pairs of angularly-aligned, longitudinally-spaced ITEV bipolar electrode pairs, each pair positioned at a different circumferential position.
Figure 13B:
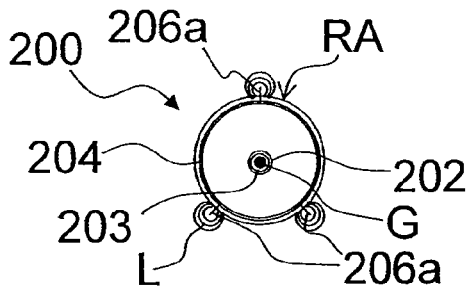
Figure 13C:
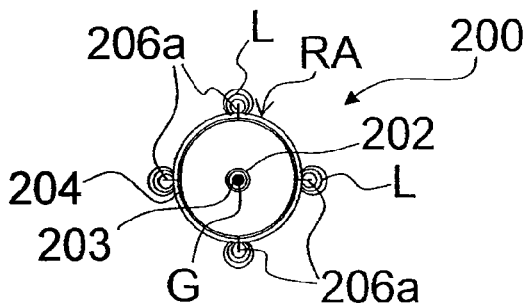

Referring now to FIGS. 13A-D, methods and apparatus for circumferential pulsed electric field modulation of target neural fibers via multiple pairs of angularly-aligned, longitudinally-spaced ITEV bipolar electrode pairs in which each electrode pair is positioned at a different circumferential position. FIGS. 13A-D illustrate several examples of the ITEV PEF system 200 along section line A-A of FIG. 12. In FIG. 13A, the ITEV PEF system 200 comprises two pairs of angularly-aligned, longitudinally-spaced bipolar electrodes 206 circumferentially positioned approximately 180° apart, as in FIG. 12. In FIG. 13B, the system 200 comprises three pairs of such bipolar electrodes spaced approximately 120° apart. In FIG. 13C, the system 200 comprises four pairs spaced roughly 90° apart, and in FIG. 13D, the system 200 comprises eight pairs spaced about 45° apart. As will be apparent, any desired number of electrode pairs may be provided. Furthermore, although the electrode pairs shown in FIGS. 13A-D have been equally circumferentially spaced, they alternatively may be circumferentially spaced at any other desired spacing, including any other desired unequal circumferential spacing.

Figure 13D:
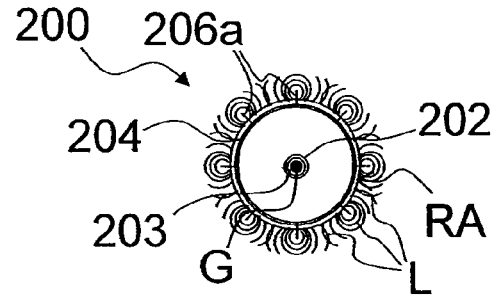

As illustrated by field lines L in FIGS. 13A-D, the tissue region affected by PEF therapy delivery across each bipolar electrode pair, e.g., the tissue region experiencing desired neuromodulation, is confined to a narrow circumferential segment of the treatment site. Providing multiple pairs of bipolar ITEV electrode pairs 206 may provide a more circumferential treatment. As seen in FIG. 13D, adding additional pairs of ITEV bipolar electrodes 206 eventually causes the circumferentially-affected segments to overlap, thereby providing full circumferential treatment. In some cases, it may be desirable to provide full circumferential treatment, while in other cases it may be desirable to provide less than complete circumferential treatment. The medical practitioner may provide any desired level of circumferential treatment and/or may utilize any desired number of circumferentially-spaced bipolar electrode pairs. Circumferential PEF therapy along a longitudinal segment of the patient's vessel may be achieved by collapsing the expansion element 204, rotating the catheter 202 a desired amount about its longitudinal axis, and then re-expanding the expansion element 204 to re-position electrode pairs 206 extravascularly for treatment of another circumferential longitudinal segment of the patient's vessel. This process can be repeated at a single longitudinal location as desired.

Figure 14A:
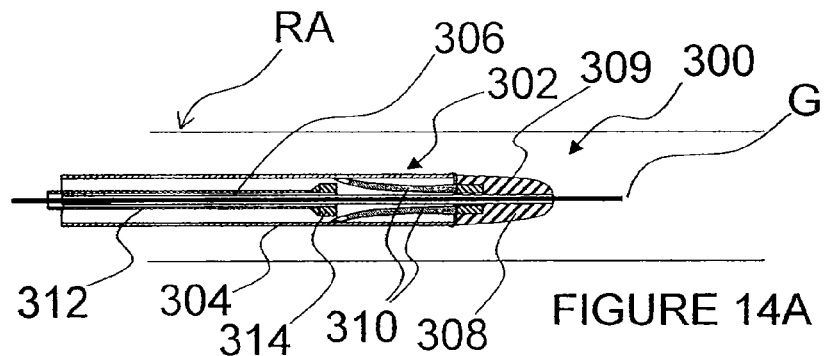
FIGS. 14A-14D are schematic side-sectional views and schematic side-views, partially in section, illustrating alternative methods and apparatus for pulsed electric field neuromodulation via electrodes positioned extravascularly via an intra-to-extravascular approach.
Figure 14B:
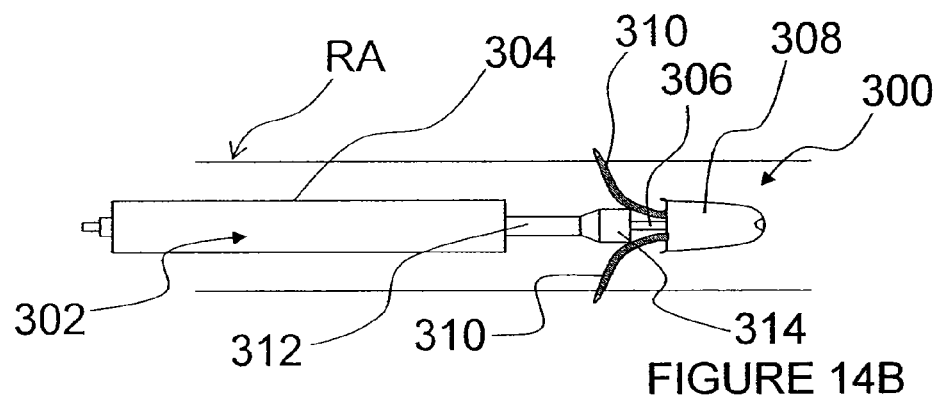

FIGS. 14A and 14B show additional ITEV PEF systems 300 that comprise a catheter 302 having an outer sheath 304, a guidewire tube 306, and an atraumatic nosecone 308. The guidewire tube 302 is coupled to and extends through or communicates with a lumen 309 of the atraumatic nosecone 308. The system 300 also includes a number of proximally-oriented ITEV needle electrodes 310 coupled to the nosecone 308 at their distal regions, and a pusher tube 312 coaxially positioned about the guidewire tube 306. The pusher tube 312 optionally has a flared tip 314, which may be relatively stiff and/or radiopaque. The electrodes 310 may be coupled to the PEF generator 50 via electrical contacts formed with or within the guidewire tube 306 (e.g., via a metallic braid, coil or wire on or near an outer diameter of the guidewire tube). The electrodes 310 may physically contact these electrical contacts to facilitate delivery of PEF therapy. In some embodiments, the flared tip 314 completes the circuit upon contacting the electrodes, as in FIG. 14B.

FIG. 14A shows the system 300 in the reduced delivery and retrieval configuration with the electrodes 310 positioned within the sheath 304. Upon intravascular placement at a treatment site, the sheath 304 is retracted and/or the guidewire tube 306 is advanced, such that the electrodes 310 are removed from the sheath 304. The electrodes 310 preferably are fabricated from an elastic material that resists deformation and applies a restoring force upon deformation. Furthermore, the electrodes 310 preferably are coupled to the nosecone 308 in a manner that biases the electrodes 310 to the reduced profile shown in FIG. 14A.

As seen in FIG. 14B, when the catheter 302 is positioned at a treatment site (e.g., within the renal artery RA), the pusher tube 312 is advanced relative to the guidewire tube 306 such that the flared tip 314 engages and elastically deforms the electrodes 310 radially outward. The electrodes 310 pierce the vessel to position the tips of the electrodes extravascularly via an ITEV approach. The catheter 302 optionally may be retracted after deformation of the electrodes 310 to engage the electrodes with the patient's vessel and place the electrodes extravascularly. PEF therapy then may proceed to achieve desired neuromodulation. Upon completion of the treatment, the pusher tube 312 is retracted relative to the guidewire tube 306 and the electrodes 310. The guidewire tube 306 is advanced slightly to release the electrodes 310 from the vessel wall. The restoring force provided by the electrodes 310 returns the electrodes 310 to the reduced at-rest profile. The sheath 304 then may be advanced relative to the guidewire tube 306, such that the needle electrodes 310 are once again positioned within the sheath 304 as in FIG. 16A for retrieval and removal from the patient.

In an additional or alternative embodiment of the apparatus of FIGS. 14A and 14B, the needle electrodes 310 may be replaced with needle housings through which the needle electrodes may be advanced. The needle housings are expanded into contact with a vessel wall, and the needle electrodes then are advanced across the vessel wall. Such advancement may be accomplished via a variety of mechanical means. For example, advancement of the pusher tube past a specified position relative to the guidewire tube, the nosecone and/or the needle housings may release a spring-loaded member that advances the needles.

Figure 14C:
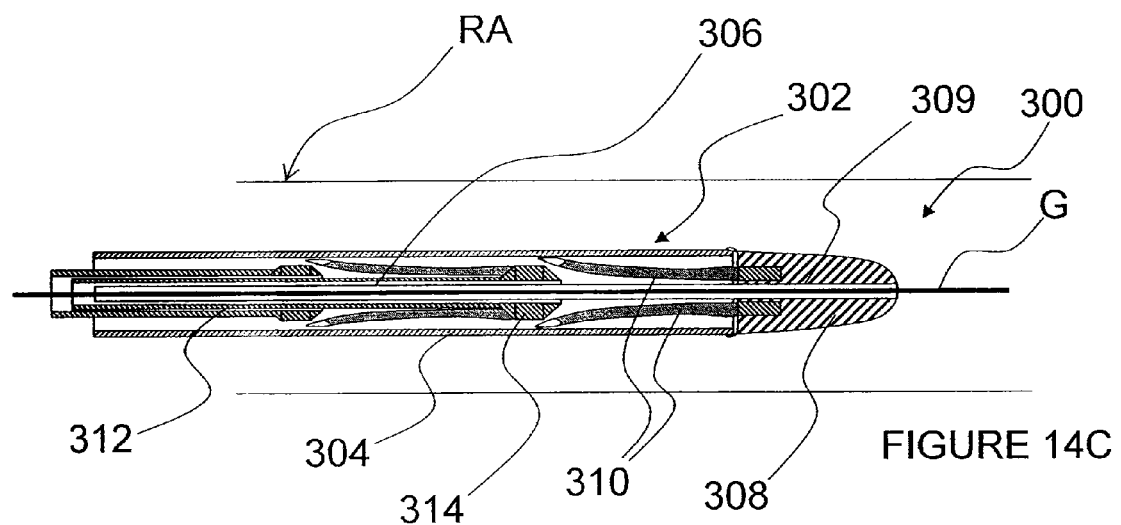
Figure 14D:
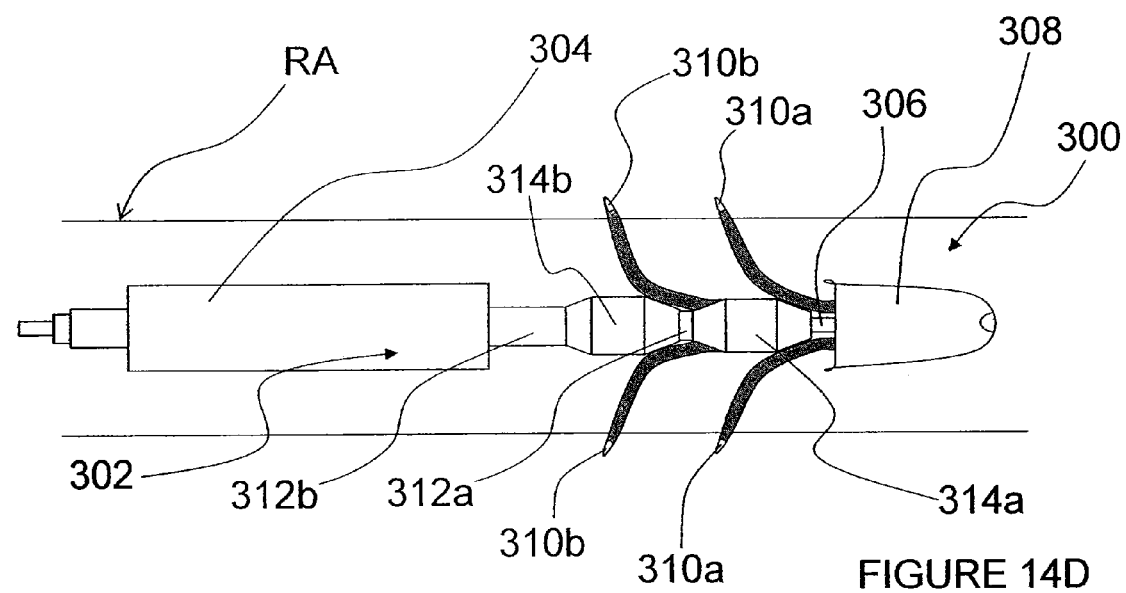

FIGS. 14C and 14D illustrate an alternative embodiment of the ITEV PEF system 300 comprising one or more longitudinally spaced pairs of bipolar electrodes. In FIGS. 14C and 14D, needle electrodes 310a are coupled to the nosecone 308, and needle electrodes 310b are coupled to a proximal region of a first flared tip 314a of a first pusher tube 312a. The system 300 further comprises a second pusher tube 312b having a second flared tip 314b. The second pusher tube 312b is coaxially disposed about the first pusher tube 312a.

Electrodes 310a and 310b form one or more longitudinally spaced pairs of bipolar electrodes. For example, electrodes 310a may comprise active electrodes and electrodes 310b comprise return electrodes, or vice versa. As seen in FIG. 14C, the electrodes may be delivered within the sheath 304. Once positioned at a treatment site, the sheath 304 may be withdrawn, and the electrodes 310 may be positioned extravascularly via an ITEV approach, as in FIG. 14D. Specifically, the first pusher tube 312a may be advanced relative to the guidewire tube 306, such that first flared tip 314a impinges upon and deforms the needle electrodes 310a. This urges the electrodes 310a across the vessel wall. Likewise, the second pusher tube 312b may be advanced relative to the first pusher tube 312a such that the second flared tip 314b impinges upon and deforms the needle electrodes 310b. This mechanism urges the electrodes 310b across the vessel wall. In the embodiment of FIGS. 14C and 14D, the flared tips 314 comprise distal profiles that provide gradual transitions for deforming the electrodes 310.

Figure 15A:
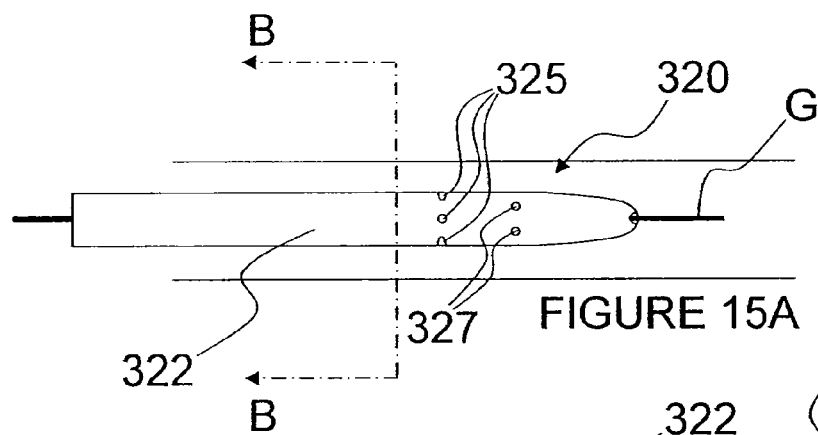
FIGS. 15A-15C are schematic side-views, partially in section, as well as a cross-sectional view along section line B-B of FIG. 15A, of further alternative methods and apparatus for pulsed electric field neuromodulation via electrodes positioned extravascularly via an intra-to-extravascular approach.
Figure 15C:
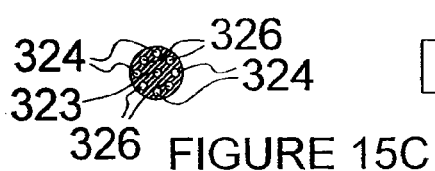
Figure 15B:
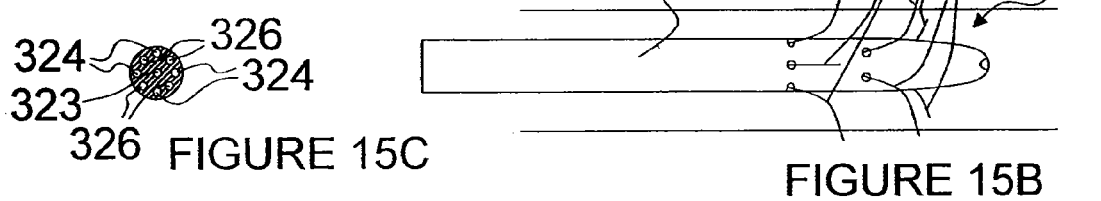

FIGS. 15A-C show examples of another ITEV PEF system 320 that comprises a catheter 322 having (a) a plurality of proximal electrode lumens 324 terminating at proximal side ports 325, (b) a plurality of distal electrode lumens 326 terminating at distal side ports 327, and (c) a guidewire lumen 323. The catheter 322 preferably comprises an equal number of proximal and distal electrode lumens. The system 320 also includes proximal needle electrodes 328 that may be advanced through the proximal electrode lumens 324 and needle electrodes 329 that may be advanced through the distal electrode lumens 326.

As illustrated in FIG. 15A, the catheter 322 may be advanced over the guidewire 321 via the lumen 323 to a treatment site within the patient's vasculature (e.g., to a treatment site within the patient's renal artery RA). During intravascular delivery, the electrodes 328 and 329 are positioned such that their non-insulated and sharpened distal regions are positioned within the lumens 324 and 326, respectively. Once positioned at a treatment site, a medical practitioner may advance the electrodes via their proximal regions that are located external to the patient. As seen in FIG. 15B, such advancement causes the distal regions of the electrodes 326 and 329 to exit side ports 325 and 327, respectively, and pierce the wall of the patient's vasculature such that the electrodes are positioned extravascularly via an ITEV approach.

The proximal electrodes 328 can be connected to PEF generator 50 as active electrodes and the distal electrodes 329 can serve as return electrodes. In this manner, the proximal and distal electrodes form bipolar electrode pairs that align PEF therapy with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Any combination of active and distal electrodes may be utilized, as desired.

When the electrodes 328 and 329 are positioned extravascularly, PEF therapy may proceed to achieve desired neuromodulation. After completion of the PEF therapy, the electrodes may be retracted within lumens 324 and 326. The catheter 322, as well as the guidewire 321 then may be removed from the patient to complete the procedure. Additionally or alternatively, the catheter may be repositioned to provide PEF therapy at another treatment site.

Figure 16A:
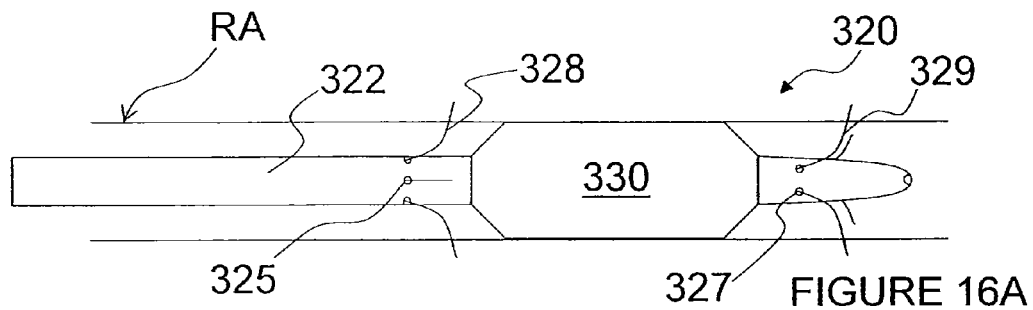
FIGS. 16A and 16B are schematic side-views of alternative embodiments of the methods and apparatus of FIG. 15.
Figure 16B:
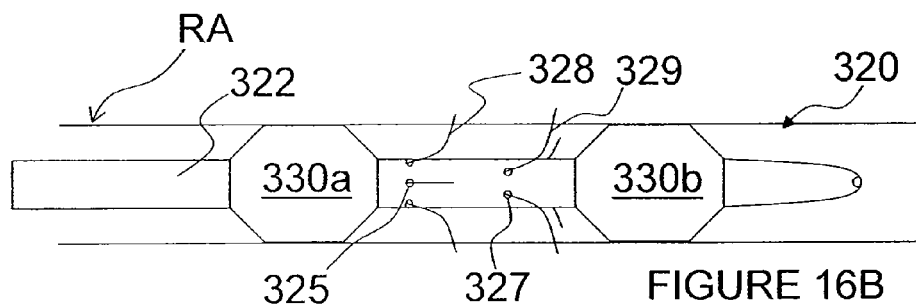

FIGS. 16A and 16B show alternative embodiments of the ITEV PEF system 320. In FIG. 16A, the catheter 322 of the system 320 further comprises an expandable centering element 330, which may comprise an inflatable balloon or an expandable basket or cage. In use, a centering element 330 may be expanded prior to deployment of the needle electrodes 328 and 329 to center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes to the same depth).

In FIG. 16A, the illustrated centering element 330 is positioned between the proximal side ports 325 and the distal side ports 327, i.e., between the delivery positions of the proximal and distal electrodes. However, it should be understood that centering element 330 additionally or alternatively may be positioned at a different location or at multiple locations along the length of catheter 322 (e.g., at a location proximal of side ports 325 and/or at a location distal of side ports 327). In FIG. 16B, the system 320 illustratively comprises a first centering element 330a positioned proximal of the proximal side ports 325 and a second centering element 330b positioned distal of the distal side ports 327.

Figure 17A:
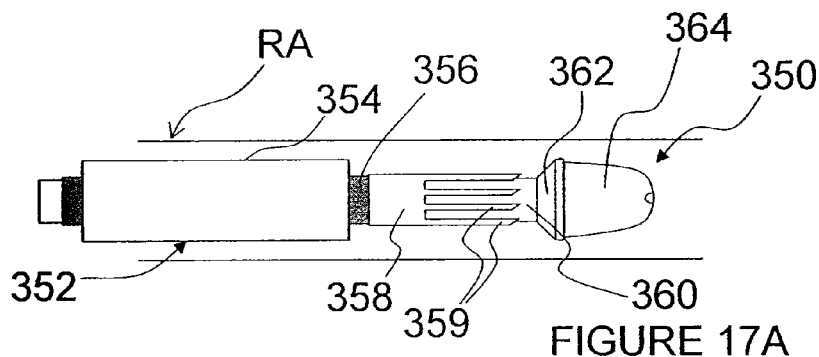
FIGS. 17A-17E are schematic side-views, partially in section, of still further methods and apparatus for pulsed electric field neuromodulation via electrodes positioned extravascularly via an intra-to-extravascular approach.
Figure 17B:
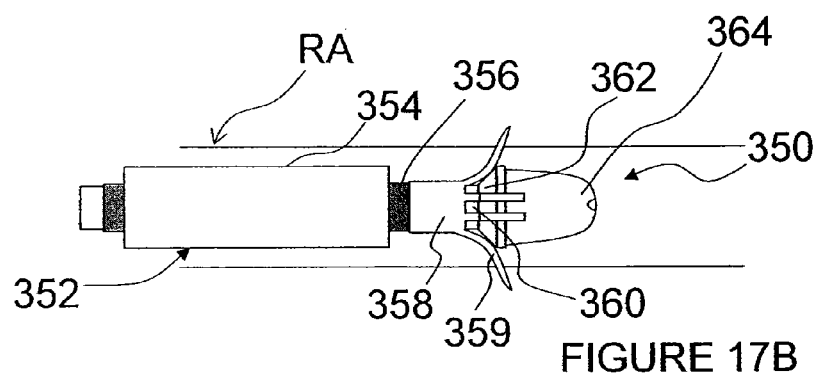

Referring now to FIGS. 17A-E, ITEV PEF systems 350 utilizing one or more hypotubes are described. In the embodiment of FIGS. 17A and 17B, the ITEV PEF system 350 comprises a catheter 352 having an outer sheath 354, an outer shaft 356, a hypotube 358 with multiple distal extensions 359, and an inner shaft 360 with a guide block 362. The inner shaft 360 terminates at an atraumatic tip 364, and a guidewire lumen preferably extends through the inner shaft and the atraumatic tip. The hypotube 358 is connected proximally to the outer shaft 356, and the outer shaft 356 is coaxially positioned over the inner shaft 360.

The hypotube 358 can have extensions 359 that may be fabricated by cutting away portions of the hypotube. The hypotube 358 may be fabricated from a conductive material, such as a metal alloy or platinum, or the hypotube may comprise a relative non-conductive material. The extensions 359 may be selectively insulated and/or non-insulated, and they may be electrically coupled to the PEF generator 50 to provide one or more extension electrodes. The extension electrodes may, for example, be etched onto the hypotube and its extensions, e.g., via a metal deposition process. Electrical contacts for energy delivery may be exposed at the tips of insulated extensions 359; alternatively, the non-insulated contacts may extend across all or part of the lengths of the extensions. Furthermore, the entire hypotube 358 may comprise an electrode when the hypotube is fabricated from a conductive material.

The extension electrode(s) 359 may be of a common polarity or may be of different polarities. When of different polarities, PEF therapy may be delivered across the electrodes in a bipolar fashion. When of common polarity, the electrodes may be utilized in a monopolar fashion, e.g., with an external ground pad. Alternatively, the catheter 352 optionally may comprise one or more additional electrodes of opposite polarity along its length that may be utilized in a bipolar fashion with the extension electrode(s) 359 of the hypotube 358. In one embodiment, the outer shaft 356 comprises at least a second hypotube along its length having extension electrode(s) that serve as the additional electrode(s) of opposite polarity and may be utilized to form spaced bipolar electrode pair(s) for delivery of the PEF therapy.

As seen in FIG. 17A, the catheter 352 may be advanced to a treatment site within a patient's vasculature, such as a treatment site within renal artery RA, using well-known percutaneous techniques (e.g., through a guide catheter). Once properly positioned, the outer sheath 354 may be retracted to expose the hypotube 358, and then the outer shaft 356 may be advanced relative to inner shaft 360 to drive the extensions 359 against the guide block 362. As seen in FIG. 17B, the guide block 362 provides a tapered transition that progressively deforms extensions 359 in an elastic or plastic manner as the outer shaft 354 is advanced relative to the inner shaft 360. This deformation directs the extensions 359 radially outward to detone the extension electrodes. Continued advancement of the outer shaft causes the extension electrodes to penetrate the vessel wall and to be positioned extravascularly via an ITEV approach. With the extension electrodes 359 positioned extravascularly, PEF therapy may proceed.

Upon completion of the PEF therapy, the extensions 359 once again may be collapsed against the outer shaft 356 for retrieval of the system 350 from the patient. If the deformation of the extensions 359 comprises elastic deformation, the outer shaft 356 may be retracted relative to the wall of renal artery RA to remove the extensions from the wall. The extensions 359 then will return to their at-rest configuration of FIG. 17A. If the deformation is plastic, then the extensions 359 may, for example, be collapsed by advancing the outer sheath 354 or a guide catheter over the outer shaft 356 such that the sheath 354 abuts the bases of the extensions 359. The outer shaft 356 then may be retracted while the sheath 354 is held stationary or advanced relative to the outer shaft to collapse the extensions 359 within the sheath 354 for retrieval of the system 350 from the patient.

Figure 17C:
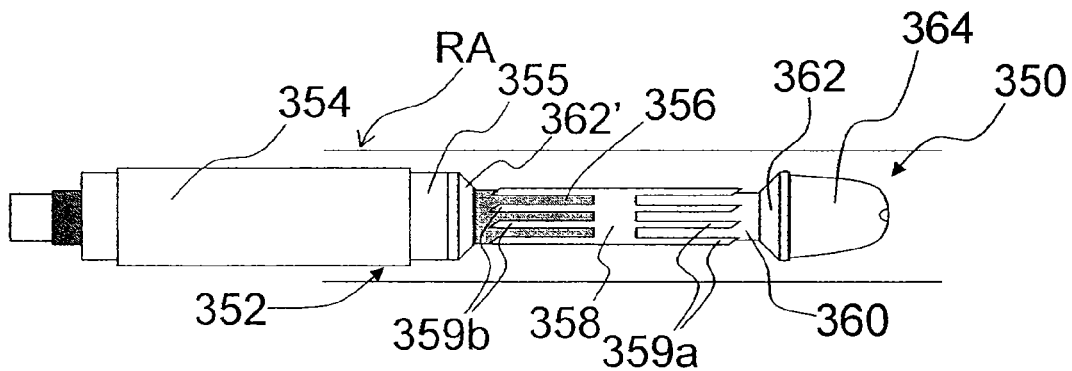
Figure 17D:
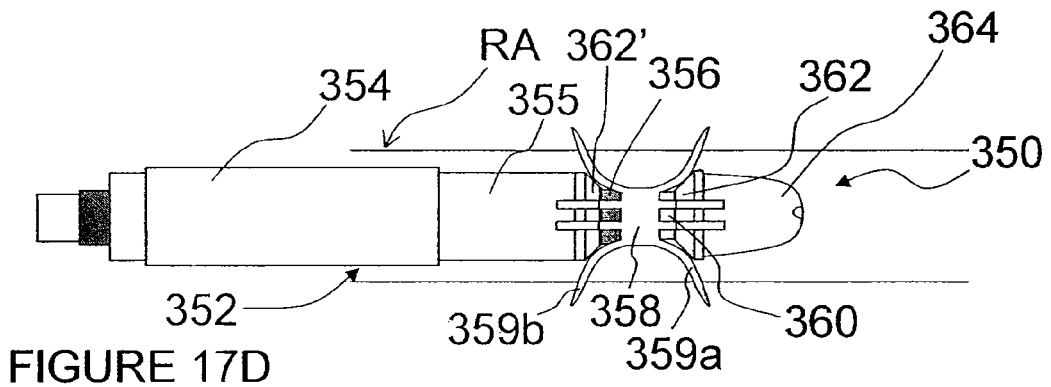

As seen in FIGS. 17C and 17D, the ITEV PEF system 350 optionally may comprise one or more longitudinally spaced pairs of ITEV electrodes. In FIGS. 17C and 17D, the hypotube 358 comprises distal extensions 359a and proximal extensions 359b. The distal extensions 359a may be deployed extravascularly in the manner described previously. For ITEV deployment of the proximal extensions 359a, the system 350 further comprises a proximal pusher tube 355 having a distally-oriented guide block 362' for deforming the proximal extensions 359b. The pusher tube 355 is coaxially disposed over the outer shaft 356, but within the outer sheath 354. As seen in FIG. 17D, the pusher tube 355 may be advanced relative to the outer shaft 356 in order to deform the proximal extensions 359b and position the extension electrodes extravascularly via an ITEV approach. The proximal and distal extension electrodes of the hypotube 358 form one or more longitudinally spaced bipolar electrode pairs.

Figure 17E:
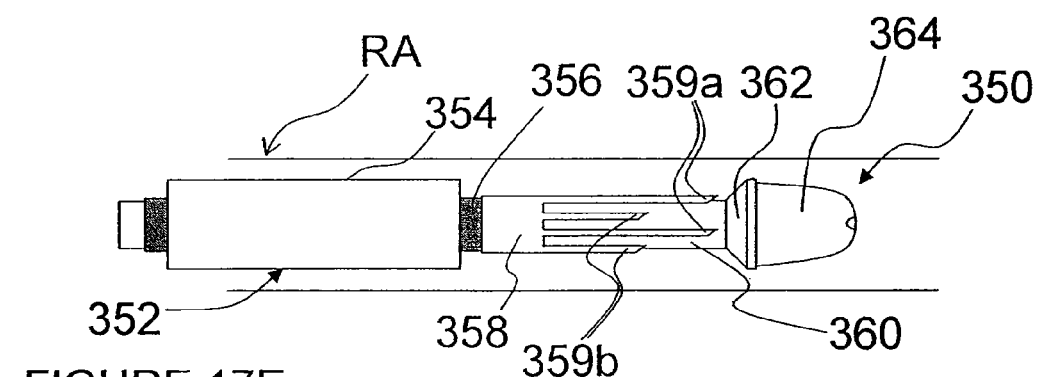

In FIG. 17E, ITEV PEF system 350 again comprises the distal extensions 359a and the proximal extensions 359b. However, in the embodiment of FIG. 17E, the proximal and distal extensions are all distally-oriented, with the distal extensions 359a being of a greater length than the proximal extensions 359b. During extravascular placement of the extensions, the additional length of the distal extensions 359a causes the distal extensions to pierce the wall of the patient's vessel more distally than do the proximal extensions 359b. In this manner, the proximal and distal extensions 359a-b are longitudinally spaced apart from one another when deployed extravascularly. After completion of extravascular PEF therapy, the distal orientation of the proximal and distal extensions 359a-b facilitates collapse and retrieval of the extensions. The outer shaft 356 may be retracted while the sheath 354 is held stationary or advanced relative to the outer shaft to collapse the extensions 359a-b within the sheath 354 for retrieval of the system 350 from the patient.

Although several examples of the ITEV systems 350 shown in FIGS. 17A-E illustrate deployment of the ITEV extension electrodes 359 via guide block(s) 362, it should be understood that the electrodes may be deployed via a variety of alternative techniques. For example, a push/pull mechanism, such as pull wire, may be utilized to deform the hypotube extensions. Alternatively, a pressure or vacuum channel may be used. An array of hypotubes and/or hypotube extension electrodes optionally may be deployed via a single deployment mechanism.

With reference to FIGS. 18A-D, alternative embodiments of the ITEV PEF system 350 are described. In FIGS. 18A-D, the guide block(s) 362 have been replaced with alternative deployment mechanisms comprising at least one expandable member, such as an inflatable balloon 366. Furthermore, the hypotube 358 has been replaced with a stent-like element 370 having the extensions 359. As will be apparent, the balloon(s) 366 alternatively may be used in combination with the hypotube 358, and/or the stent-like element 370 alternatively may be used in combination with the guide block(s) 362.

As with the hypotube 358, the stent-like element 370 may be completely conductive and may serve as a unitary electrode. Alternatively, the stent-like element 370 may be fabricated from a relatively insulating material with electrode contacts that are etched or deposited onto the element and/or its extensions. A variety of electrode configurations may be provided. Furthermore, the multiple elements 370 (or a combination of hypotubes 358 and elements 370) may be provided. In addition or as an alternative to the deployment mechanisms illustrated in FIG. 18, the extensions 359 may be deployed via other deployment mechanisms, such as push/pull mechanisms (e.g., a pull wire) or a pressure/vacuum channel.

Figure 18A:
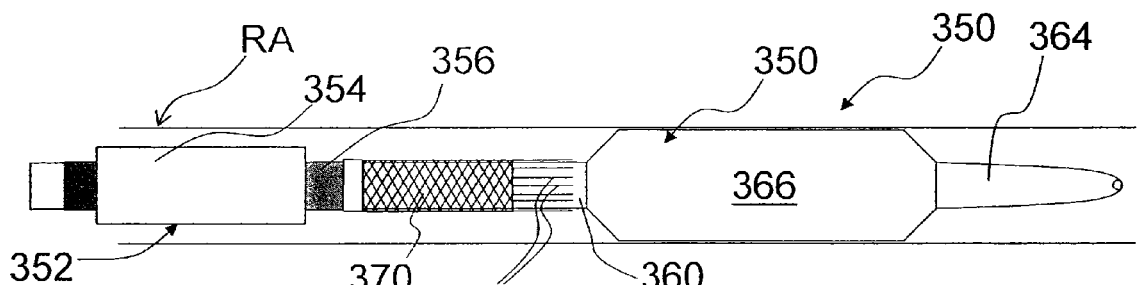
FIGS. 18A-18D are schematic side-views, partially in section, of alternative embodiments of the methods and apparatus of FIG. 17.
Figure 18B:
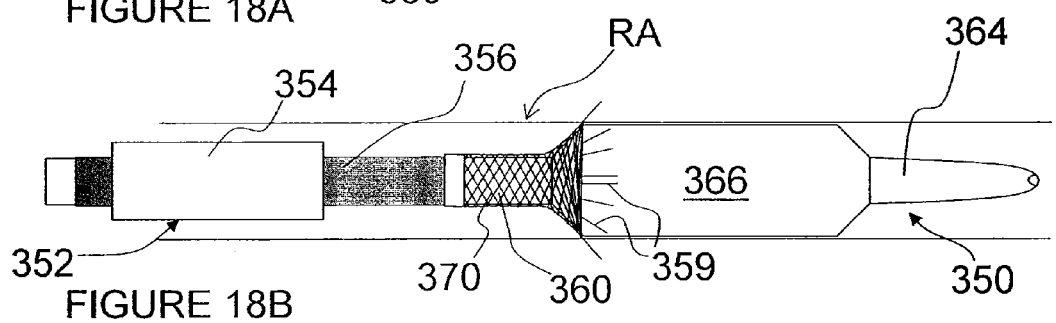

As seen in the embodiment of FIGS. 18A and 18B, the system 350 may be positioned at a treatment site, and the balloon 366 coupled to the inner shaft 360 may be inflated into contact with the vessel wall. As seen in FIG. 18A, the inflated balloon 366 centers the system 350 within the vessel and provides a tapered guide path that provides a smooth transition for deformation of the extensions 359 of the stent-like element 370 during ITEV placement of the extension electrodes. As seen in FIG. 18B, the outer shaft 356 may be advanced relative to the inner shaft 360 such that the extensions 359 begin to deform about the balloon and are directed radially outward. This deformation optionally may be assisted via additional deployment mechanisms, such as pull-wires, to begin deformation of the extensions 359. Continued advancement of the outer shaft 356 relative to the inner shaft causes the extensions 359 to pierce the vessel wall so that the ends of the extension electrodes 359 are positioned extravascularly via an ITEV approach.

Figure 18C:
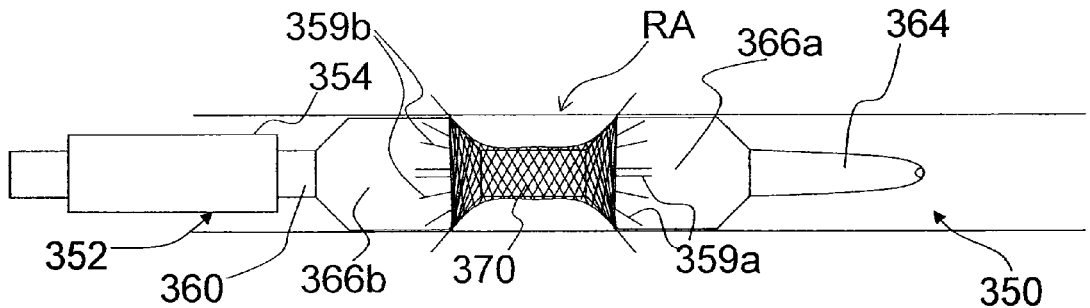

As seen in FIG. 18C, the stent-like element 370 may comprise longitudinally spaced extensions 359a and 359b to provide longitudinally spaced bipolar electrode pairs. In FIG. 18C, the inner shaft 360 comprises distal and proximal expandable elements, illustratively a distal balloon 366a and a proximal balloon 366b. The stent-like element 370 is positioned between the proximal and distal balloon, with the extensions 359a and 359b overlapping the distal and proximal balloons 366a-b, respectively. This overlap obviates a need for the outer shaft 356 shown in FIGS. 18A and 18B. ITEV placement of the extension electrodes 359a-b is achieved by inflating balloons 366.

Figure 18D:
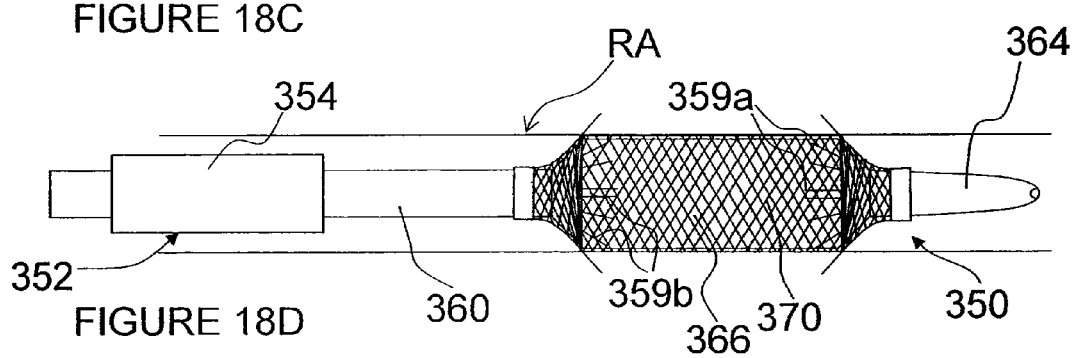

As seen in FIG. 18D, the stent-like element 370 with proximal and/or distal extensions 359 may be positioned over an expandable element, such as inflatable balloon 366. The expandable element 370 may be coupled to the shaft 360 proximally and/or distally (e.g., at a distal collar 368a and at a proximal collar 368b). At least one of the collars 368a or 368b is slidingly coupled to the shaft 360 to facilitate expansion of the expandable element 370 during expansion of the balloon 366. As with the embodiment of FIG. 18C, the positioning of the expandable element 370 relative to the balloon 366 obviates a need for an outer shaft. Rather, ITEV placement of the extension electrodes is achieved by inflating the balloon 366.

Figures 19A, 19B:
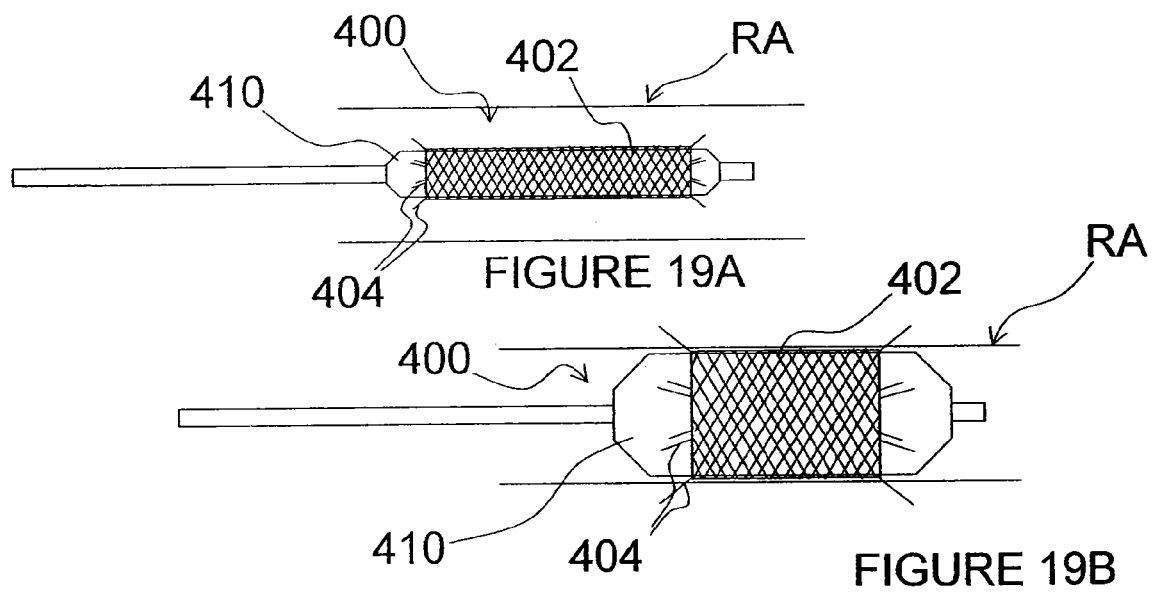
FIGS. 19A and 19B are schematic side-views, partially in section, of methods and apparatus for pulsed electric field neuromodulation comprising a stent having electrodes configured for intra-to-extravascular placement.

Referring now to FIGS. 19A and 19B, an alternative ITEV PEF 400 system is described comprising an expandable stent. The ITEV PEF system 400 comprises a stent 402 having extensions 404 configured to pierce the wall of a patient's vasculature upon expansion of the stent. The extensions 404 may be proximal and distal extensions that form longitudinally spaced bipolar electrode pairs. Additionally, the extensions 404 can be electrically coupled to the PEF generator 50 and utilized as extravascular electrodes for delivery of PEF therapy.

As seen in FIG. 19A, a stent 402 may be delivered to an intravascular treatment site, such as a site within renal artery RA, in a reduced profile configuration. The stent 402 may, for example, be positioned on a delivery and deployment catheter, such as a balloon catheter 410, during advancement and deployment at the treatment site. The catheter 410 may (temporarily) electrically couple the stent to the PEF generator. As seen in FIG. 19B, when the stent 402 is properly positioned at the treatment site, it may be deployed to contact the vessel wall (e.g., via the deployment catheter) such that extensions 404 penetrate the wall of the vessel. This accordingly positions the extension electrodes extravascularly via an ITEV approach. PEF therapy then may proceed, and upon completion the catheter 410 may be collapsed and removed from the patient.

The system 400 facilitates repeat PEF therapy at a later time. For example, by temporarily electrically re-coupling the catheter 410 or some other electrical coupling element to the stent 402, the system 400 can repeat PEF therapy as desired. When utilized to achieve renal denervation, such repeat therapy may, for example, be repeated upon evidence of re-innervation of the renal(s).

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. An apparatus, comprising:
    an electric field generator;
    a catheter comprising an elongated shaft; and
    at least one electrode electrically coupled to the electric field generator and carried by the elongated shaft, the electrode configured for intravascular delivery and extravascular placement via an intra-to-extravascular approach,
    wherein the electrode is configured for extravascular delivery of an electric field to one or more target neural fibers that innervate a kidney of a patient to reduce neural activity along the neural fibers, and
    wherein a distal portion of the elongated shaft is configured to be within the patient and a proximal portion of the elongated shaft is configured to be external to the patient during delivery of the electric field.

2. The apparatus of claim 1, wherein the electrode comprises at least one bipolar electrode pair having a first electrode and a second electrode, and wherein the bipolar electrode pair is coupled to the electric field generator.

3. The apparatus of claim 2, wherein the apparatus is configured for extravascular delivery of the electric field across the bipolar electrode pair.

4. The apparatus of claim 2, wherein the first electrode is configured for extravascular placement via an intra-to-extravascular approach, and the second electrode is configured for intravascular placement.

5. The apparatus of claim 4, wherein the first electrode comprises an active electrode and the second electrode comprises a return electrode.

6. The apparatus of claim 2, wherein both the first electrode and the second electrode are configured for extravascular placement via an intra-to-extravascular approach.

7. The apparatus of claim 2, wherein the first electrode and the second electrode are longitudinally spaced apart from one another in a deployed configuration.

8. The apparatus of claim 2, wherein the first electrode and the second electrode are angularly-aligned with one another relative to a circumference of a patient's vasculature.

9. The apparatus of claim 1, further comprising an external ground pad, wherein the electrode is configured for monopolar extravascular delivery of the electric field to reduce neural activity along the neural fibers.

10. The apparatus of claim 1, further comprising a piercing element configured for intravascular delivery, wherein the piercing element is configured to pierce a wall of vasculature of a patient from within the vasculature.

11. The apparatus of claim 10, wherein the electrode is configured for extravascular placement through a wall piercing created with the piercing element.

12. The apparatus of claim 10, wherein the electrode comprises the piercing element.

13. The apparatus of claim 10, wherein the piercing element comprises a needle or cannula.

14. The apparatus of claim 13, wherein the electrode is configured for extravascular placement through a lumen of the needle.

15. The apparatus of claim 1, wherein the catheter further comprises an expandable element configured for intravascular delivery in a low profile configuration and for expansion to an expanded deployed configuration at a target location at least proximate to the target neural fibers, and wherein the electrode is carried by the expandable element of the catheter.

16. The apparatus of claim 1, wherein the apparatus is configured for extravascular infusion of agents.

17. The apparatus of claim 16, wherein the apparatus is configured for extravascular infusion of agents that enhance delivery of the electric field to the target neural fibers or provide protective effects.

18. A method, comprising:
  intravascularly advancing at least one electrode to a treatment site within a blood vessel of a patient;
  passing a portion of the electrode through at least a portion of a wall of the blood vessel to position the electrode at an extravascular location via an intra-to-extravascular approach; and
  extravascularly delivering an electric field via the electrode to one or more target neural fibers along the blood vessel that innervate a kidney of the patient to reduce neural activity along the neural fibers.

19. The method of claim 18 wherein extravascularly delivering an electric field via the electrode to one or more target neural fibers further comprises extravascularly delivering RF energy via the electrode to reduce neural activity along the neural fibers.

20. The method of claim 18 wherein extravascularly delivering an electric field via the electrode to one or more target neural fibers further comprises extravascularly delivering thermal energy via the electrode to reduce neural activity along the neural fibers.

21. The method of claim 18 wherein extravascularly delivering an electric field via the electrode to one or more target neural fibers further comprises extravascularly delivering ablative energy via the electrode to reduce neural activity along the neural fibers.

22. The method of claim 18 wherein extravascularly delivering an electric field via the electrode to one or more target neural fibers further comprises extravascularly delivering a pulsed electric field via the electrode to reduce neural activity along the neural fibers.

23. The method of claim 18 wherein intravascularly advancing at least one electrode to a treatment site within the blood vessel comprises intravascularly moving the electrode to a treatment site within a renal blood vessel of the patient.

24. The method of claim 18 wherein intravascularly advancing at least one electrode to a treatment site within the blood vessel comprises intravascularly moving the electrode to a treatment site within a renal artery of the patient.

25. The method of claim 18 wherein passing a portion of the electrode through at least a portion of a wall of the blood vessel further comprises piercing the wall of the blood vessel and advancing the electrode through the wall piercing.

26. The method of claim 25 wherein piercing the wall of the blood vessel further comprises forcing the electrode through the wall of the blood vessel.

27. The method of claim 18 wherein intravascularly advancing at least one electrode to a treatment site within the blood vessel further comprises advancing at least one bipolar electrode pair to the treatment site within the blood vessel.

28. The method of claim 27 wherein:
  passing a portion of the electrode through at least a portion of a wall of the blood vessel to position the electrode at an extravascular location further comprises moving the bipolar electrode pair extravascularly; and
  extravascularly delivering an electric field via the electrode further comprises extravascularly delivering the electric field across the bipolar electrode pair.

29. The method of claim 27 wherein passing a portion of the electrode through at least a portion of a wall of the blood vessel to position the electrode at an extravascular location further comprises positioning a first electrode of the bipolar electrode pair at the extravascular location and positioning a second electrode of the bipolar electrode pair at an intravascular location.

30. The method of claim 18 wherein extravascularly delivering an electric field via the electrode to one or more target neural fibers along the blood vessel that innervate a kidney of the patient comprises extravascularly delivering the electric field to a renal nerve of the patient to inhibit neural activity to and from the kidney of the patient.

* * * * *